(12) United States Patent
Alexandre et al.

(10) Patent No.: US 8,580,499 B2
(45) Date of Patent: Nov. 12, 2013

(54) DETECTION AND/OR QUANTIFICATION METHOD OF TARGET MOLECULES ON A SOLID SUPPORT

(75) Inventors: Isabelle Alexandre, Haltinne (BE); Heinz Koehn, Hamburg (DE); Jose Remacle, Jambes (BE); Sven De Roeck, Brussels (BE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 13/107,353

(22) Filed: May 13, 2011

(65) Prior Publication Data

US 2011/0281775 A1 Nov. 17, 2011

Related U.S. Application Data

(60) Division of application No. 12/357,265, filed on Jan. 21, 2009, now Pat. No. 7,993,840, which is a continuation-in-part of application No. PCT/EP2008/059404, filed on Jul. 17, 2008.

(30) Foreign Application Priority Data

Jul. 20, 2007 (EP) ..................... 07112900

(51) Int. Cl.
*C12Q 1/68* (2006.01)
*C12M 1/34* (2006.01)
*C12P 19/34* (2006.01)

(52) U.S. Cl.
USPC ...... 435/6.1; 435/91.2; 435/287.2; 435/288.7

(58) Field of Classification Search
None
See application file for complete search history.

(56) References Cited

U.S. PATENT DOCUMENTS 6,108,463 A * 8/2000 Herron et al. ................ 385/12
2005/0059069 A1 3/2005 Suzuki et al.

FOREIGN PATENT DOCUMENTS

| EP | 1411133 A1 * | 4/2004 |
| WO | 9320240 A1 | 10/1993 |
| WO | 03023377 A1 | 3/2003 |
| WO | 2006135437 A3 | 12/2006 |

OTHER PUBLICATIONS

Knorr et al. PCR Methods and Applications (1993) 3: 73-74.*
Von Nickisch-Rosenegk, et al., "On-chip PCR Amplification of Very Long Templates Using Immobilized Primers on Glassy Surfaces," Biosensors and Bioelectronics, vol. 20, pp. 1491-1498 (2005).
Lehr, H-P, et al., "Real-Time Detection of Nucleic Acid Interactions by Total Internal Reflection Fluorescence," Analytical Chemistry, American Chemical Society, vol. 75, No. 10, pp. 2414-2420 (2003) XP001170913.
International Search Report of PCT/EP2008/059404 dated Nov. 18, 2008.
U.S. Appl. No. 12/357,265—Restriction Requirement dated Sep. 29, 2009.
U.S. Appl. No. 12/357,265—Non-final office action dated Jan. 22, 2010.
U.S. Appl. No. 12/357,265—Non-final office action dated Nov. 8, 2010.
U.S. Appl. No. 12/357,265—Notice of Allowance dated Apr. 1, 2011.

* cited by examiner

*Primary Examiner* — Angela M Bertagna
(74) *Attorney, Agent, or Firm* — Morgan, Lewis & Bockius LLP

(57) ABSTRACT

The present invention relates to a method and device for detecting and/or quantifying one or multiple target molecules present in a solution by quantifying online their binding on specific capture molecules immobilized at different locations (spots) of a surface of an optically transparent solid support without substantial detection of target molecules present in solution. The present invention allows multiple target assays to be performed in a simultaneous detection. More particularly, the invention comprises detecting in real-time the hybridization between capture DNA molecules present on a micro-array and target polynucleotides present in solution. The invention is also related to real-time PCR of multiple targets on a micro-array.

12 Claims, 14 Drawing Sheets

A B C D

DETECTION AND/OR QUANTIFICATION METHOD OF TARGET MOLECULES ON A SOLID SUPPORT

CROSS REFERENCE TO RELATED APPLICATIONS

The present application is a divisional of U.S. application Ser. No. 12/357,265, filed Jan. 21, 2009 (now U.S. Pat. No. 7,993,840), which is a continuation-in-part of International Application No. PCT/EP2008/059404, filed Jul. 17, 2008, and claims priority from European Application No. EP 07112900.1, filed Jul. 20, 2007, each of which is hereby incorporated by reference in its entirety.

FIELD OF THE INVENTION

The present invention relates to a method, apparatus and kit for detecting and/or quantifying one or multiple target molecules present in a solution by quantifying online their binding on specific capture molecules immobilized on a surface of a solid support without substantial detection of target molecules present in solution. The present invention allows multiple target assays to be performed in a simultaneous detection. More particularly, the invention comprises detecting in real-time the hybridization between capture DNA molecules present on a micro-array and target polynucleotides present in solution. Finally the invention is also related to real-time PCR of multiple targets.

DESCRIPTION OF THE RELATED ART

To obtain the maximum information about the smallest amount of sample is one of the major objectives of analytical science. This holds particularly true in molecular biology and in all molecular based life science where there is a demand for a highly parallel analysis. Micro-array technology is one answer to this demand. It enables massive parallel determinations and multiple measurements for binding events to be performed simultaneously in the same solution. Micro-arrays usually consist of many microscopic spots each one containing identical molecules, i.e. nucleic acids or proteins acting as capture molecules. The number of spots can vary from less than one hundred to several thousand. The molecules are immobilized to a solid support by an attachment preferably by covalent link. The primary task of a micro-array experiment is to simultaneously detect many binding events.

Because of its high sensitivity, fluorescence is used in most applications as a label to detect the binding events. Prior to carrying out the experiment, the sample must be labelled by means of a suitable fluorochrome. Binding is achieved in a separate incubation step and the final result is obtained after appropriately washing and drying of the micro-array. Micro-array readers usually acquire information about the fluorescence intensity at a given time of the binding process that would ideally be the time after arriving at the thermodynamic equilibrium. However, under the conventional conditions employed in the chip experiments, thermodynamic equilibrium is difficult to obtain and not reached at the same time for the different targets, being present in a biological sample at different concentrations that may vary by several logs scale, because of several limitations such as the difference in the binding kinetics, the diffusion constant and the concentration of capture molecules. So in a fixed experiment setting, it is difficult to settle down experimental conditions in which the amount of the targets bound to their capture molecules would be directly proportional to the solution concentrations.

The quantification step which follows the binding step on the micro-array is made after several steps of washing and implies that some essential information regarding the process such as the kinetics of the binding reaction is definitely lost. One solution to the problem to overcome the variability on the binding efficiency of the concentration dependence of the different targets present in a single sample, is to obtain the data on binding reaction in real-time for each individual target present in the solution.

Bier and Schmidt (2004, Anal. Bioanal. Chem., 378, 52-53) teach the necessity to bring together a fluid-handling approach combined with an integrated detection scheme to make possible real-time analysis on micro-arrays. The method is based on the following up an enzyme reaction in real-time on spots carrying labeled double stranded DNA. The immobilized DNA serves both as a binding receptor for the enzyme and as substrate to be cleaved by a restriction enzyme. After addition of the cofactor $Mg^{2+}$, the spots in which the DNA is cleaved by the enzyme are identified by the decrease in the fluorescence intensity (negative assay) at a given location.

Bier and Kleinjung (2001, Fresenium J. Anal. Chem., 371, 151-156) propose to measure the hybridization kinetics mainly in the dissociation phase by obtaining melting curves for each spot of the micro-array. Following the same idea, U.S. Pat. No. 6,589,740 discloses means to detect hybridization reaction of fluorescent targets upon chips. Images of the reaction are taken at predetermined timings while running a washing solution into the container and while changing the temperature of the biochip according to a predetermined time pattern. Melting curves are obtained by washing the chip at increasing temperatures. As the temperature rose, sample DNA with weaker binding ability begin to dissociate from the probe DNA and the dissociated sample DNA is removed from the spots with the washing solution. Accordingly, the amount of hybridized fluorescence-labeled sample DNA decreases with lapse of time, and so as the fluorescent intensity.

The WO 06/053769 proposes a method for real-time detection of a target being in solution while reacting on its corresponding immobilized capture molecule. The method relies on the use of excitation light for exciting the bound target and assayed for the emitted light. The method takes party of the confocal scanning method which allows obtaining a better signal from the bound target where the excitation light is focused than from the target present in the solution. While the results are positive and convincing, the limitation of the method is the high background of the assay.

The U.S. Pat. No. 6,416,951 teaches another method for measuring in real-time the kinetics of hybridization of RNA with a polynucleotide probe. The kinetics are measured by either hybridizing in the presence of an intercalation dye and recording a change in the spectroscopic properties of the dye as hybridizing proceeds, or incorporating a label in the RNA or the probe, attaching the non-labeled molecule to a solid support, generating an evanescent wave in the proximity of the attached molecule and recording the increase in a signal generated by interaction of the evanescent wave with the label, as hybridization proceeds.

WO 99/57310A2 uses support made of a matrix in the form of dots, each dot of the matrix representing an individual species of molecule. The matrix is made of a gel-like support. To each dot corresponds an optical lens for detection. The sample is allowed to flow thought the microfluidic structure and the binding of the target is carried out with real-time measurement of the hybridization. The fluidic helps the detection since the solution does not stay into contact with the capture molecule by flow through the matrix and the proposed detection is performed after washing.

Stimpson et al. (1995, PNAS, 92, 6379-83) describe the use of a particulate label on a target DNA which acts as a light-scattering source when illuminated by the evanescent wave of the wave guide and only the label bound to the surface generates a signal. WO 99/20789 also discloses a method based the assay of scatter light produced by a particulate label adsorbed at multiple DNA capture zones placed on a wave guide surface. The light scattering is produced by an evanescence wave created by a wave guide. Since an evanescent wave only extends a few hundred nanometers from the waveguide surface, the unbound/dissociated label does not scatter light and a wash step is not required. Desorption of the light-scattering label was followed in real-time. Evanescence is associated with Total Internal Reflection Fluorescence (TIRF) of the excitation light.

Lehr et al (2003, Anal. Chem., 75, 2414-2420) propose to use TIRF in order to follow the hybridization of target probes (Real-time detection) on a micro-array. The targets are obtained in a PCR cycler and are made single stranded by removing the second strand by a special treatment. The targets are labeled with biotin and after hybridization, they are made fluorescent by incubation with the streptavidin Cy5. Lehr et al. (2003, Sensors and Actuators, 92, 303-314) developed a mathematical model and they propose an optical setup for the use of the TIRF detection method to follow the kinetic of hybridization of a fluorescent molecule such as Cy5. The documents do not mention nor cite the detection of amplicons during the PCR cycles by hybridization onto immobilized probes.

In the same line, U.S. Pat. No. 5,633,724 provides method and apparatus for detecting a target substance in a pixel array using a total internal reflection (TIR) member having a TIR surface on which a pixel array is located and using evanescence excitation of the target substance.

Evanescence associated with the TIR is a method which can discriminate between the bound to the non bound target but its application to array measurement is made difficult due to the fact that one requirement is that the same amount of bound target located at different locations has to give the same signal. This requires the same excitation, meaning the same light. To obtain uniform light on the entire surface where the different captures are located is a difficult task since by principle, the evanescence excitation requires the illumination light to go through inside the support as TIR, and so the light reaches the surface by the side of the support on which the probes are located or by a very tangential angle.

WO 03/023377 describes an alternative method to evanescence to discriminate between a luminescent medium close to the substrate from a medium further away from the substrate. The method uses a detector adapted to detect light emitted through the lower surface of the substrate at angles greater than the critical angle of the medium/substrate interface. However, the physical setting of the invention does not provide imaging the analyzed surface onto the detector surface but a one point detection.

In WO 2004/044171, the support is used as a waveguide in order to detect the light emitted by the target bound to capture molecules on the surface of a support. The bound molecules are excited by a moving light source and the emitted fluorescent light is collected at the edge of the support after having moved in the support as total internal reflection. The fact that the light goes through the support as internal reflection forces the detection to be performed after illumination of parts of the surface of the support by a moving illumination device and to reconstitute the pattern of the emission on the surface thereafter.

WO 03/052421 describes an electro-chemical analysis device for monitoring nucleic acids detection. The device comprises a biosensor, which is formed of a gold electrode having a plurality of probes attached thereto and an integrated thermal sensor. Analysis of molecular interaction is achieved at the biosensor site based on electrical detection.

The US patent application publication number 2005/0191686, describes a method for detection of PCR product in real-time by the detection of the presence of the nanoparticles incorporated into the amplicons by electrochemical detection. Wie et al. (2003, Biosensors and Bioelectronics, 18, 1157-1163) propose to monitor DNA hybridization on alkyl modified silicon surface through real-time capacitance measurement.

WO 02/099386 proposes a microcalorimetry detection based on the heat change during the binding of the target on capture molecules.

The document WO 01/27327, which is hereby incorporated by reference herein in its entirety, is related to a way to perform multiple PCR using a special device of 2 solid surfaces, one of the two surfaces contains immobilized specific oligonucleotides used as primers and the other one is an array of wells in which the PCR can take place (cfr for example FIG. 15). The resulting amplified product present in the well solution is followed in fluorescence using for example the intercalating agent SYBR Green (FIGS. 20 and 21). The document mentions the possibility to capture the amplicons on immobilized capture molecules but this capture is not done as real-time detection along the PCR cycles but is a post-PCR detection using a fluorescent microscope. The document does not mention nor cited the possible hybridization of the amplicons on immobilized capture molecules, their detection and the repetition of the process of PCR cycles and further detection on immobilized probes.

As seen by this review, there have been different methodologies proposed for performing a real-time detection of a target while it is binding on corresponding immobilized capture molecule. There is however a need to propose a new simple method for quantifying the binding of target molecules to capture molecules while the targets are present in solution, obviating the shortcomings associated with prior art methods. Specifically, the method should be simple to carry out, quantitative, cost effective and compatible with the PCR.

SUMMARY OF THE INVENTION

The aim of the invention is to provide a specific detection of targets by their specific binding on immobilized capture molecules while the targets are present in the solution. Detection of the different targets is achieved by detection of their presence in specific locations where they are bound on the surface. The present invention provides a solution to the difficult problem of detection in one assay for the presence of different targets by their identification and their quantification while being present in the solution.

The method allows detection and/or quantification of different target molecules being bound at different locations (spots) of a surface of an optically transparent solid support having a refractive index n1 by specific interaction with capture molecules being immobilized on the solid support surface, said solid support being in contact with a solution having refractive index n2, whereby n1>n2 and wherein the target molecules are in contact with the capture molecules, said method comprising the steps of a) illuminating homogeneously the surface of the support on which the target molecules are bound, thereby causing homogeneous excitation of the target molecule and b) detecting simultaneously light emitted from the target molecule in at least four different locations (spots) in the following way:

collecting the emitted light through a side of said support which is inclined relative to the surface of the support on which the target molecules are bound, focusing the emitted light by a lens on a detector surface which is positioned at an observation angle θobin relative to the normal to the said solid support surface in the support, such that $90°>θobin>\sin^{-1}(n2/n1)$, obtaining an image of at least 4 different locations spatially separated on the solid support and being spatially discriminated onto the surface of the detector.

The above method is preferably carried out for the detection of a target bound to a capture molecule present on a surface of the solid support while being present in the solution. Preferably, the spots are spatially distant in a two dimensional pattern. Preferably the spots are arranged in the form of an array and the detected image is formed of at least 4 and preferably at least 15, and even more preferably at least 20 and even more preferably at least 50 spots having immobilized capture molecules. Even more preferably, the spots are in a regular pattern, for example as 2×2, 2×3, 2×4, 2×5 or 2×10; 3×3, 3×4, 3×5, 3×8, 3×10, 4×5, 4×10, 5×8, 10×10 and the like. Generally, the number of spots is about 500 or less, and—for practical reasons—about 100 or less. The obtained image has preferably the same corresponding pattern as the array surface and is preferably reshaded into an identical geometrical regular pattern for analysis and/quantification. The solution is preferably an aqueous solution having a refractive index of about 1.33.

The present invention is especially useful to follow the kinetic of binding of a target present in a solution on its capture molecule being immobilized on the surface of a support. Applications are numerous.

A preferred application is to obtain a gene expression pattern by the detection of the presence of cDNA to their capture molecules.

The above method is also preferably carried out for the detection of amplicons on a solid support in presence of the labeled amplicons in solution. The present invention is useful to detect, identify and/or quantify one or multiple genome sequences during their amplification by PCR (Real-time PCR). The present invention allows simultaneous detection and/or identification and/or quantification of the amplicons to be carried out while hybridized to specific immobilized capture molecules during the PCR process and in the presence of labeled amplicons in solution.

In another embodiment the invention provides a device in which the present method is performed comprising: an optically transparent solid support having refractive index higher than 1.33 and a thickness of at least 1 mm and preferably at least 3 mm and even more preferably 5 mm that comprises at least four target molecules bound on capture molecules present at defined locations (spot) on said solid support surface (bound target molecule) and a chamber being formed on the surface of the said solid support covering the bound capture molecules having a top wall with a thickness of 1 mm or lower and wherein said support having two surfaces inclined relative to the surface of the support on which the capture molecules are bound, one being optically transparent and used for collecting the light emitted from the location of the capture molecules in the forbidden angle (θobin) and inclined by an angle of between 90 and 60° compared to the solid support surface and the other one opposite preferably being black or covered with a color being black or covered with a color having an absorption corresponding to the wavelength of the emitted light said device also having a closing system.

The invention also provides a kit comprising a device according to the invention comprising a micro-array having at least four capture probes corresponding to the target nucleic acid sequences to be detected and an amplification composition for performing a PCR including at least one primer pair, a thermostable DNA polymerase, a hot start PCR amplification system, and a plurality of dNTPs.

In another embodiment the invention provides an apparatus for carrying out the process of the invention requiring:

an optically transparent solid support having refractive index n1 that comprises at least four target molecules bound on capture molecules present at defined locations (spot) on said solid support surface (bound target molecule) and a chamber being formed on the surface of the said solid support covering the bound capture molecules and wherein the refractive index of the solid support is higher than about 1.33, a light source to produce a light beam which is capable of homogeneous illumination of the surface of the support on which the target molecules are bound, a lens located on the emitted light path between the surface of the support on which the target molecules are bound and a detector, a detector for measuring light emitted from the target molecules in at least four different locations (spots) as an image onto the surface of detector, said emitted light being collected through a side of said support which is inclined relative to the surface of the support on which the target molecules are bound, said detector being positioned at an observation angle θobin relative to the normal to the solid support surface in the support, such that $90°>θobin>\sin^{-1}(n2/1.33)$.

The invention in a preferred embodiment relates to the process as described above, for performing a real time PCR wherein an image is obtained from an array of at least 4 spatially distant spots, the spots are spatially distant in two dimensions, the image being obtained from an array in a closed chamber and the image being obtained by either scanning lines (rows) of spots, or preferably by taking a digital picture of the whole array.

Hence, the present invention relates to a method for performing real time PCR in a closed device by performing PCR amplification and detection of the amplified targets in the said closed device comprising an optically transparent solid support having a refractive index n1 and a surface on which are capture molecules immobilized in different locations and a solution present in the said closed device and having a refractive index n2, whereby n1>n2, said method comprising the steps of:

a) performing the PCR amplification of the targets in the solution present in the closed device and detecting and/or quantifying the presence of the targets formed after or during at least one cycle by;

b) detecting the presence of the targets bound to their specific capture molecules in the following way;

illuminating homogeneously the surface of the support on which the target molecules are bound, thereby causing homogeneous excitation of the target molecule;

detecting simultaneously the light emitted from at least 4 different locations by;

collecting the emitted light through a side of said support which is inclined relative to the surface of the support on which the target molecules are bound;

focusing the emitted light by a lens on a detector surface which is positioned at an observation angle θobin relative to the normal to the said solid support surface in the support, such that $90° > \theta_{obin} > \sin^{-1}(n2/n1)$;

obtaining an image of at least 4 different locations (spots) being spatially discriminated onto the surface of the detector.

detecting and/or quantifying the signal resulting from the binding of the said target nucleotide sequences (or their fragments) to their corresponding capture probes at the different locations upon the surface of the solid support and;

c) Processing the data obtained in at least one thermal cycle in order to detect and/or quantify the amount of nucleotide molecule present in the solution before the amplification.

Preferably, the detection of the targets is performed during or after at least 3 and more preferably at least 5 PCR cycles.

The detection is preferably performed by acquisition of a single image pixel for the overall surface having at least one bound target and immobilized capture molecules in the form of an array having at least 4 and preferably 20 and even more preferably 50 spots being spatially disposed in a two dimensional pattern.

In a preferred embodiment, in the method, detection is performed by obtaining a picture [or: pixel information] of all spots simultaneously.

In a preferred embodiment, in the method, the captor surface of the detector is mechanically tilted relative to the emitted light direction.

The angle θc out is linked to the angle θc by the following relations:

n1 sin(α)=n3 sin(θc out), where α is the angle formed by the normal (15) and the side of the transparent support (16) and n3 is the refractive index of the medium where the CCD camera is placed, typically air (n3=1)

Having in this example: α=(90°−θc), the relation between θc and θc out becomes:

$$n1 \sin(90-\theta c) = n1 \cos(\theta c) = n3 \sin(\theta c \text{ out})$$

Thus: θc out=Arcsin (n1/n3 cos(θc))

If n1=1.5, n2=1.33 and n3=1, then θc=62.4° and θc out=44.7°

In this case, the observation angle of the CCD camera outside the solid support must follow the following relation: 0°<θob out<44.7.

Figure 2:
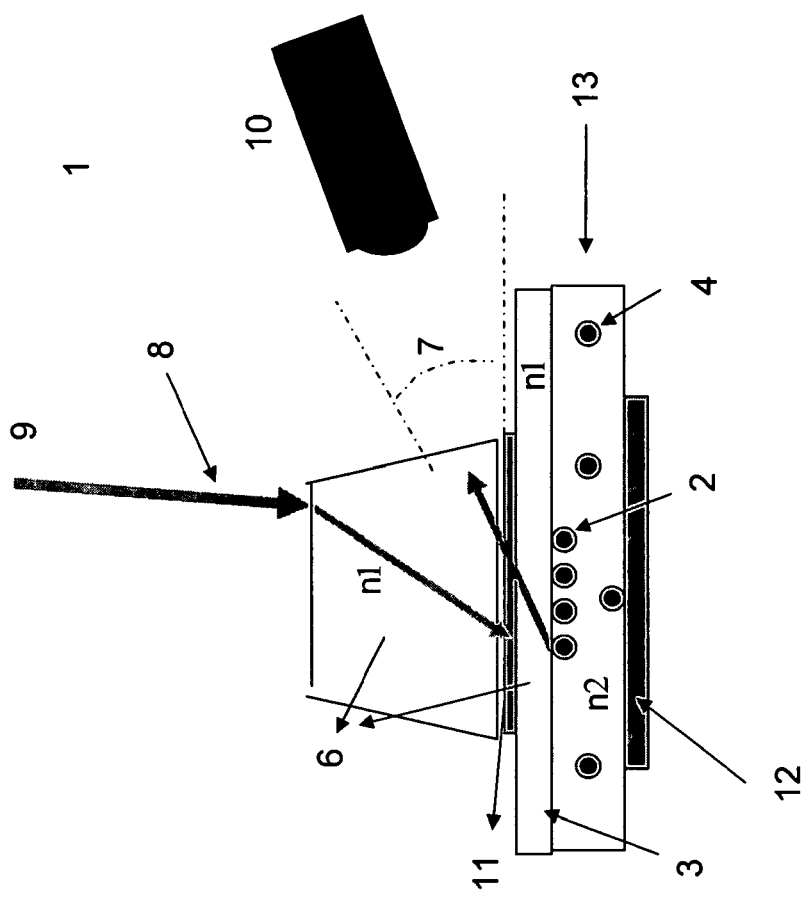

FIG. 2 represents another device (1) according to the invention. Target molecules (2) are either bound (bound target molecule) on capture molecules present on an optically transparent inner surface (3) of the closed device or present in a solution (soluble target molecule) (4) which is in contact with said inner surface and which is contained in a chamber (13). The required thickness of solid support suitable for detection in a forbidden angle is obtained by joining two solid supports (a glass slide and a prism) of the same composition (6) being separated by a material (11) having a refractive index (n3=1.47 for glycerol) close to the refractive index of said solid support (n1=1.5 for glass). The two solid supports (6) have a refractive index (n1=1.5 for glass) higher than refractive index of aqueous solution (n2=1.33) contained in the chamber (13). The solid support is illuminated by a light beam (8) from a light source (9). Signal from bound target molecules is measured with a camera (10) located within the forbidden angle (7). The lower surface of the solid support comprises a heating device (12).

Figure 3:
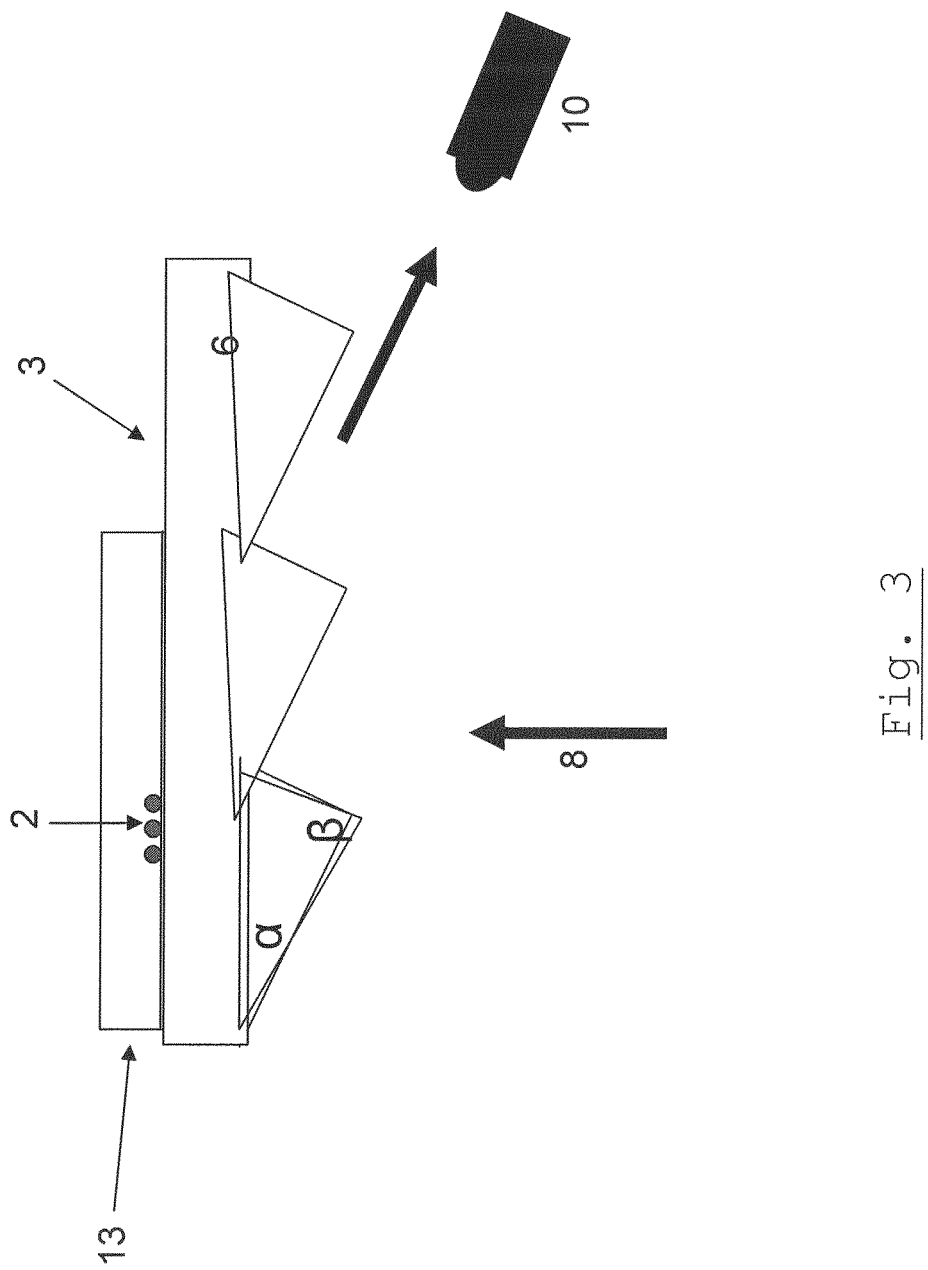

FIG. 3 represents a simplified device according to the invention incorporating ridge channel structures at the bottom of the solid support (6) being a slide for performing detection according to the invention. The top surface (3) is used for making the micro-array and bears a chamber (13) contained the bound target molecules (2). The illumination and detection are performed according to the same principle as provided in FIG. 2. β is the angle of the ridge.

Figure 4:
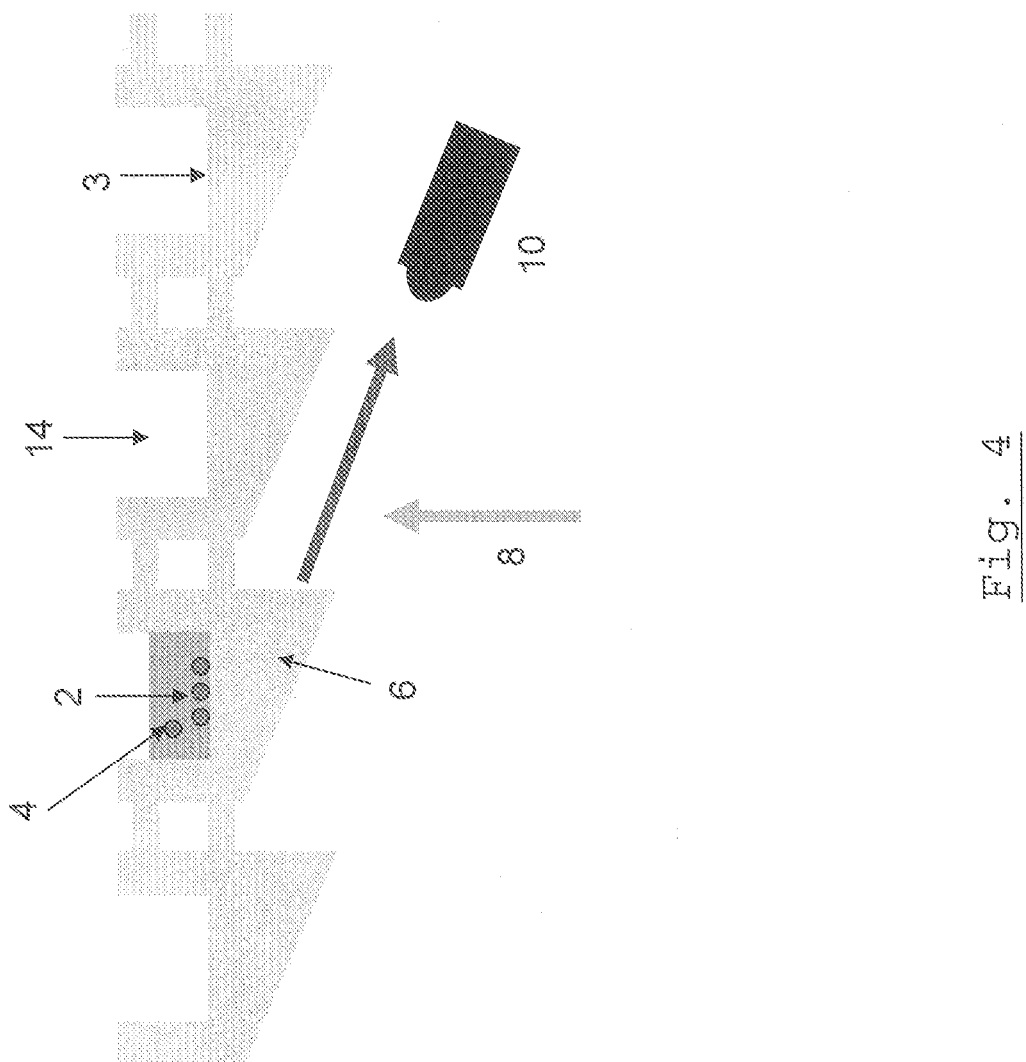

FIG. 4 represents a simplified device according to the invention incorporating ridge channel structures at the bottom of the solid support (6) being a multi-well plate. The device possesses a ridge channel structure at the bottom of each well (14) to individualize the detection according to the well. The bottom surface (3) of the well (14) is used for making the binding between the target and the capture molecule preferably in the form of an array. The well contains bound (2) and soluble (4) target molecules.

Figure 5:
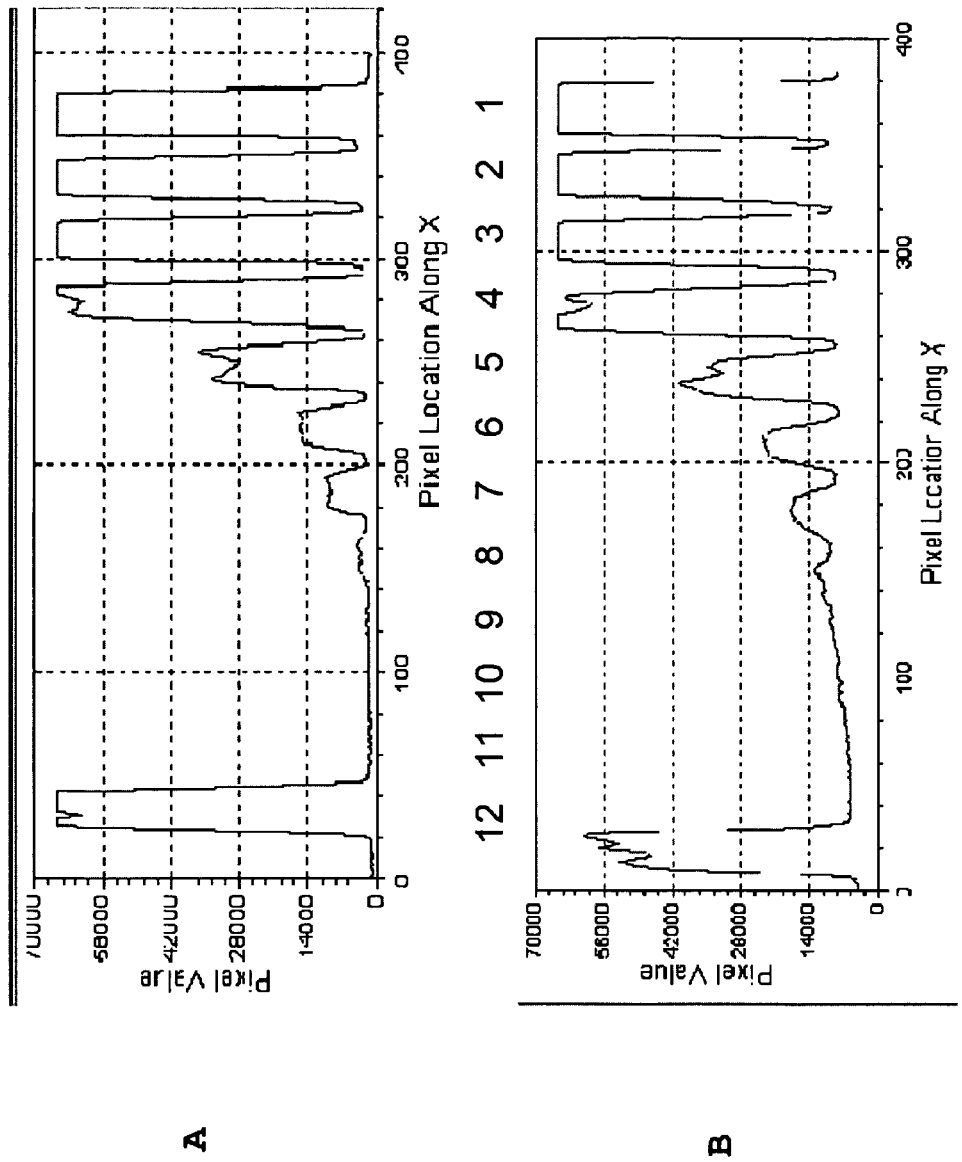

FIG. 5 shows the detection according to the design of FIG. 2 of an array of immobilized Cy3 labeled aminated polynucleotides capture molecules having been spotted at different concentrations. The reading is made in absence of solution (A) or in presence of 2 μM of Cy3 polynucleotides solution (B) in the chamber. The array (6×12) contained 12 columns spotted with Cy3 probe solution having concentrations of 3000 nM (columns 1 and 12), 1000 nM (2), 750 nM (3), 500 nM (4), 250 nM (5), 100 nM (6), 50 nM (7), 10 nM (8), 0 nM (9). The columns 10 and 11 were spotted with unlabeled probes. The 6 rows are the values of replicates of spots. The figure gives the scanning of one spot of each column obtained after detection in the forbidden angle. See example 1 for experimental details.

Figure 6:
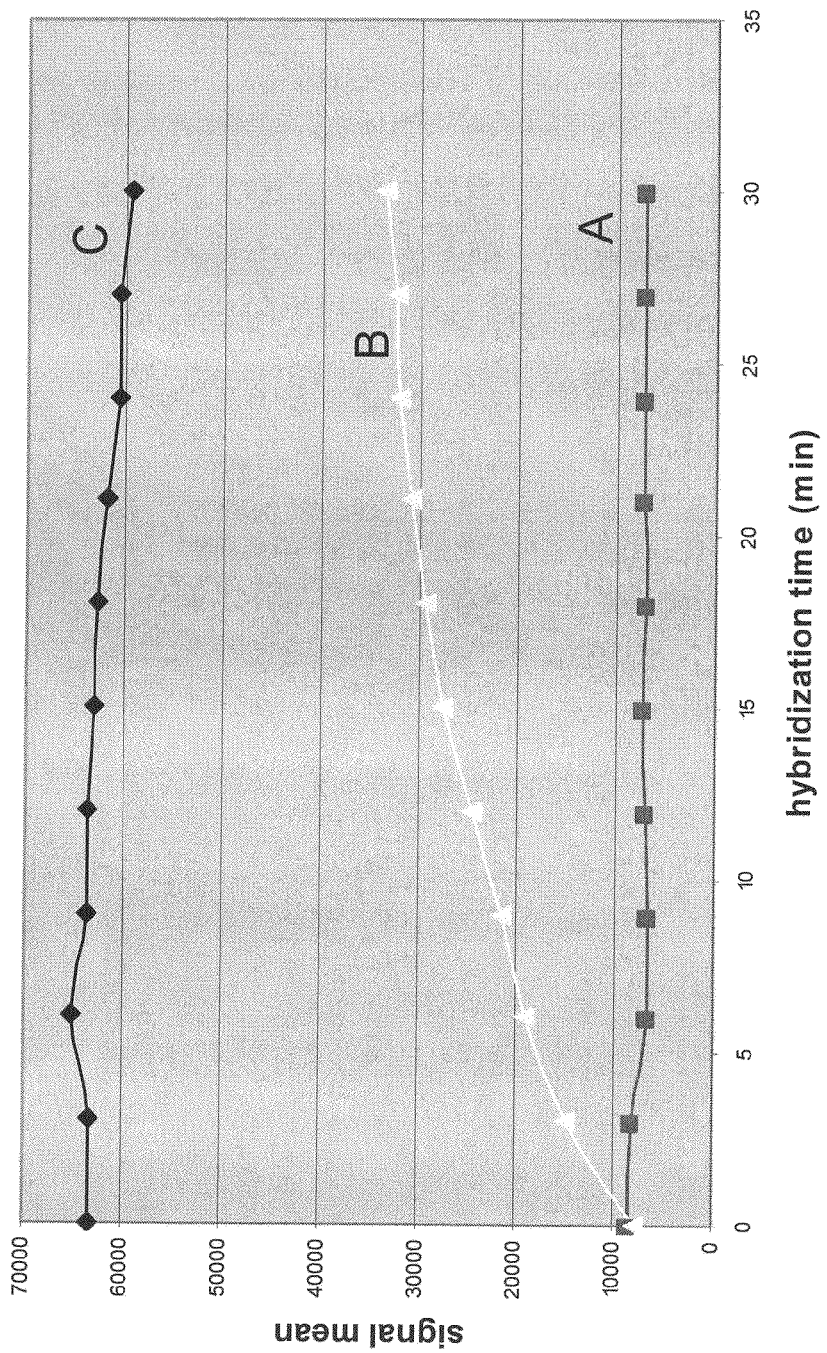

FIG. 6 presents the online detection according to the design of FIG. 2 of the hybridization of Cy5 labeled amplicons from S. aureus on their specific capture molecules (B). The detection is performed in the presence of the amplicons being present in the solution during the assay. The figure also shows the signal obtained on a capture probe being a negative hybridization control (A) and signal of a spotted Cy5 probes (C). See example 2 for experimental details.

Figure 7:
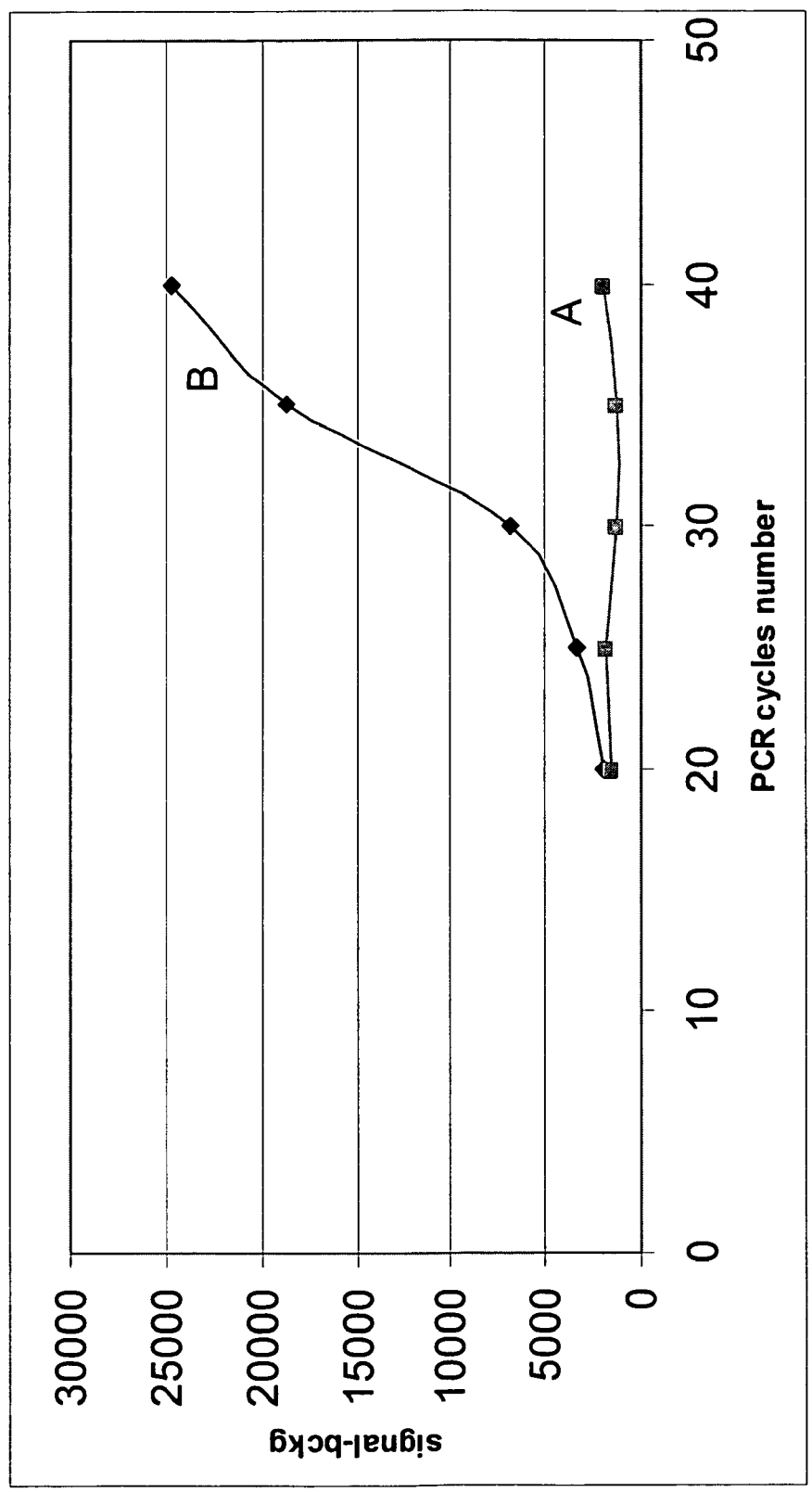

FIG. 7 presents the amplification and detection according to the design of FIG. 2 of amplicons from S. aureus on their specific capture molecules (B) along with the PCR cycles. The data give the detection values of the amplicons after 2 min incubation and the data are presented as a function of the PCR cycles. The figure also shows the signal obtained on a capture probe being a negative hybridization control (A). See example 3 for experimental details.

Figure 8:
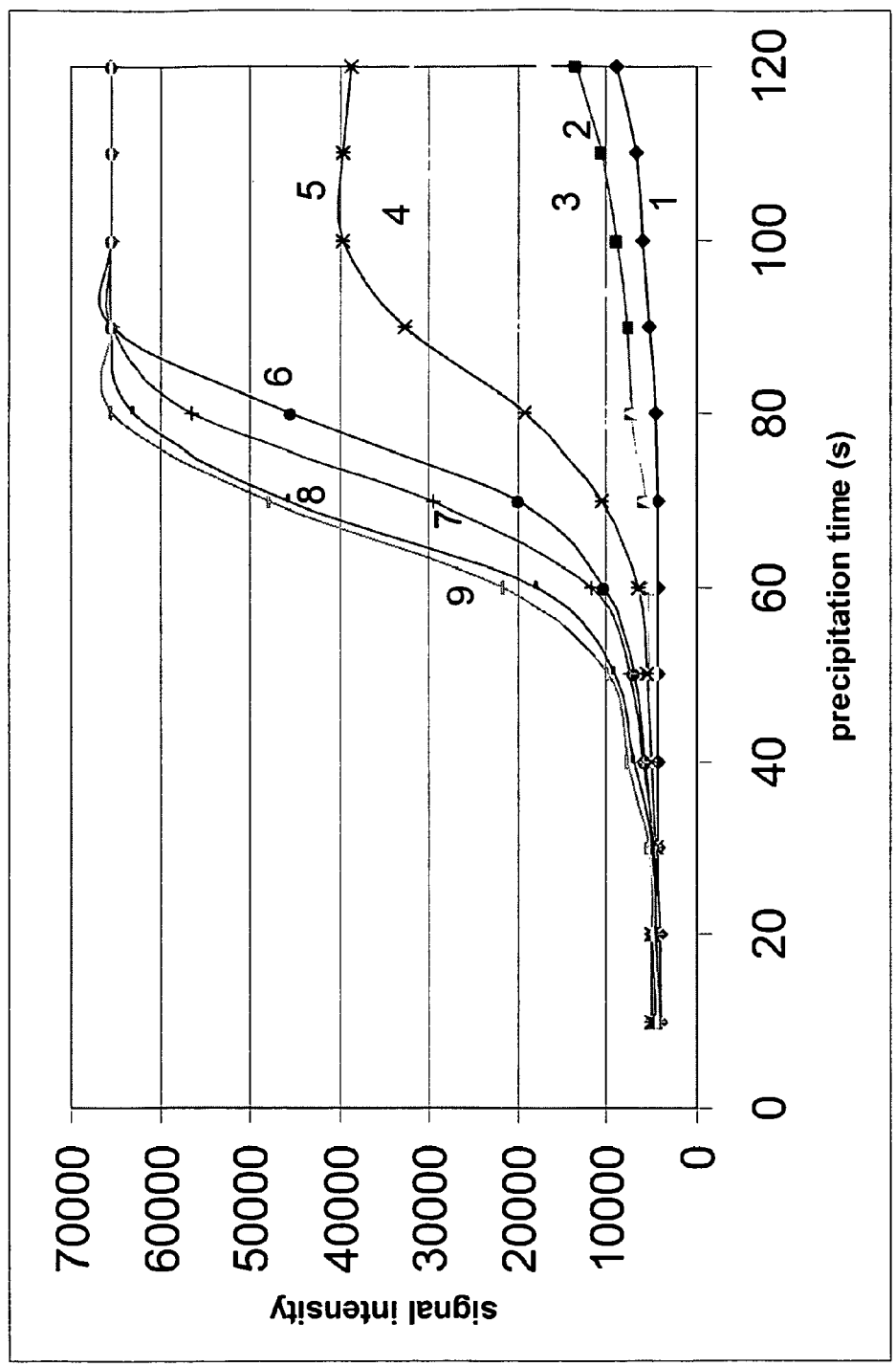

FIG. 8 presents the kinetic of silver precipitation on DNA probes spotted at different concentrations ranging from 1 to 400 nM according to the design of FIG. 2. The biotinylated probes were labeled with gold particles before being incubated with the silver enhancement reagent SILVER- QUANT® (Eppendorf, Hambourg, Germany). The signals were then followed during this enhancement reaction with time on all spots and the images obtained simultaneously for all spots present on the same array. The data give the detection values of the spotted DNA every 10 sec until 120 sec incubation. Concentrations of the spotted solution: 1 (1 nM), 2 (2 nM), 3 (4 nM), 4 (10 nM), 5 (20 nM), 6 (40 nM), 6 (40 nM), 7 (100 nM), 8 (200 nM), 9 (400 nM). See example 4 for experimental details.

Figure 9:
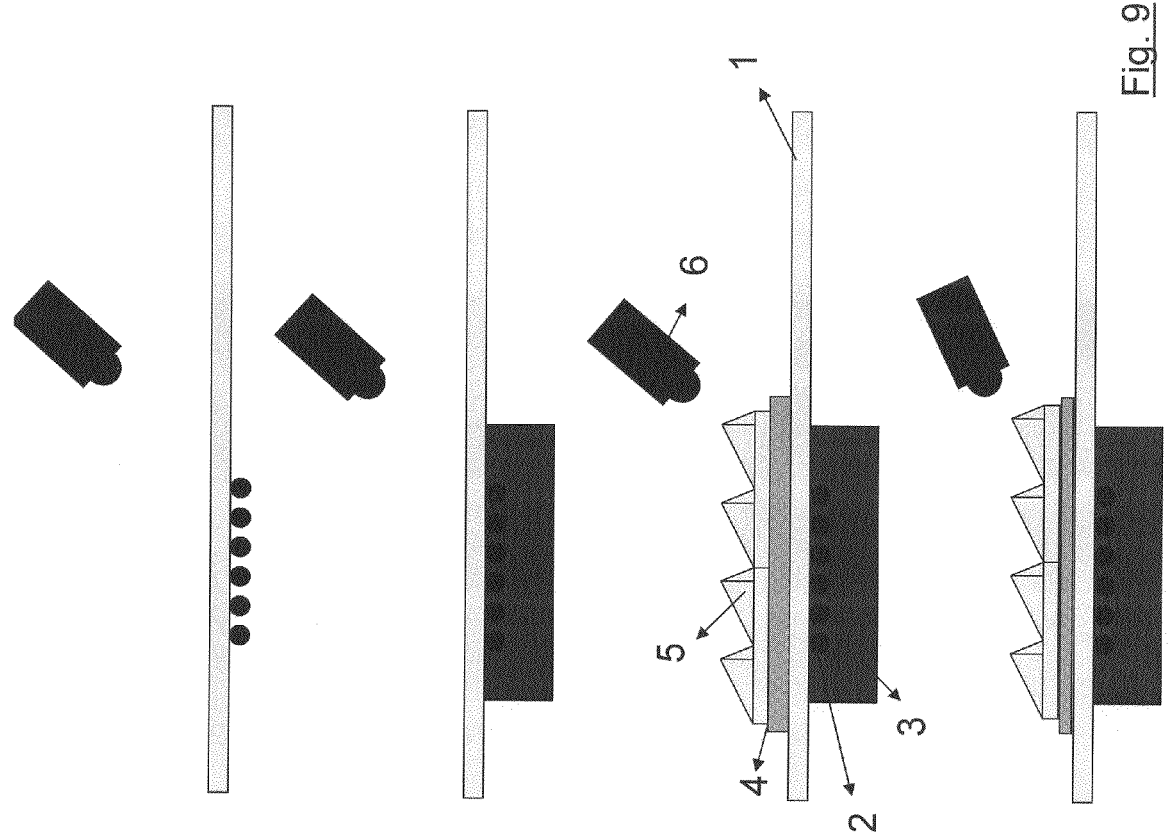
Figure 9:
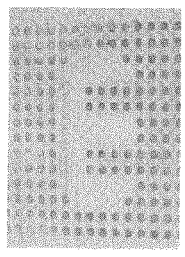
Figure 9:
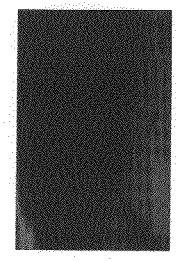
Figure 9:
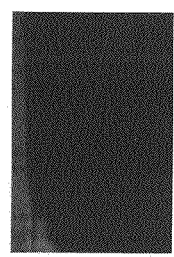
Figure 9:
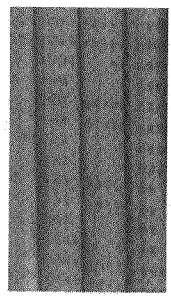

FIG. 9 illustrates the use of a ridged slide in a specific embodiment of the present invention.

On one side of glass slide 1 is an array 2. Medium 3 is in contact with slide 1 at the side of array 2.

FIG. 9A shows the pattern obtained with detector 6, which is positioned at an angle of 40° relative to the normal to slide 1, after labeling of the probes with SILVERQUANT® (a proprietary labeling technique available from Eppendorf, Hamburg, Germany).

FIG. 9B shows the pattern obtained with the same setup when chamber 3 is filled with an aniline blue solution. The pattern of the spots shows very poor contrast FIG. 9C shows the set-up of FIGS. 9A and 9B to which a ridged slide 5 is added at the observation side of glass slide 1. A glycerol layer 4 is present between glass slide 1 and ridged slide 5 to ensure optimum optical contact between the two slides. The refractive index of glycerol (n=1.47) is virtually identical to the refractive index of the two slides (n=1.52). FIG. 9C, being obtained with an observation angle of 40°, also shows a pattern having poor contrast.

FIG. 9D shows the set-up of FIG. 9C, but with the detector 6 moved to an observation angle of 65°, which is within the forbidden angle. The array is clearly visible even in the presence of high concentration of colored molecule in the solution. In this experiment, there was no correction for the focus of the image. See example 5 for experimental details.

Figure 10:
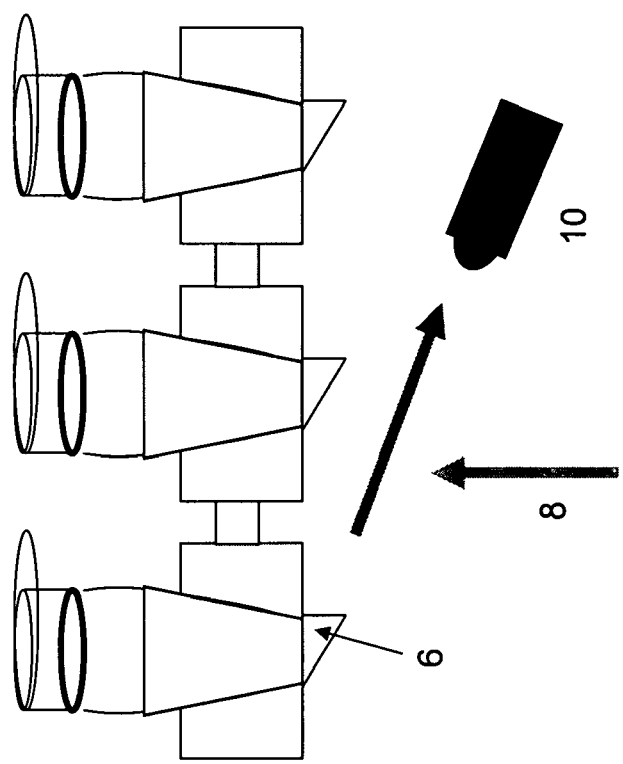

FIG. 10 represents a simplified device according to the invention incorporating a ridge channel structure at the bottom of the solid support (6) being a single tube. The device possesses a ridge channel structure at the bottom of each tube to individualize the detection according to the tube. A series of tubes may be used in parallel.

Figure 11:
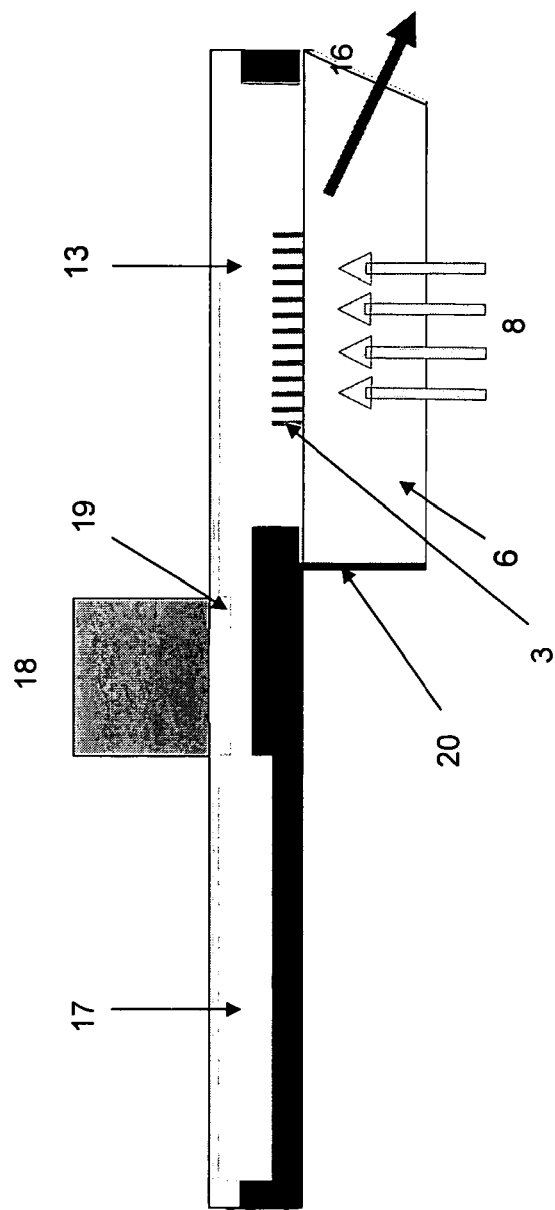

FIG. 11 represents a preferred device. The device comprises a filling inlet which is then close by a screwing cap (18). The device has a thin chamber (17) and an array chamber (13) comprising a transparent optical solid support (6) and a surface on which are bound the capture molecules (3). The bound target molecules are homogeneously illuminated by a light beam (8) through the optical support (6) and the emitted light is capture through a slightly tilted side surface (16). The opposite side surface (20) of the optical support is black. The device also contains spurs (19) between the two chambers and the inlet chamber.

Figure 12:
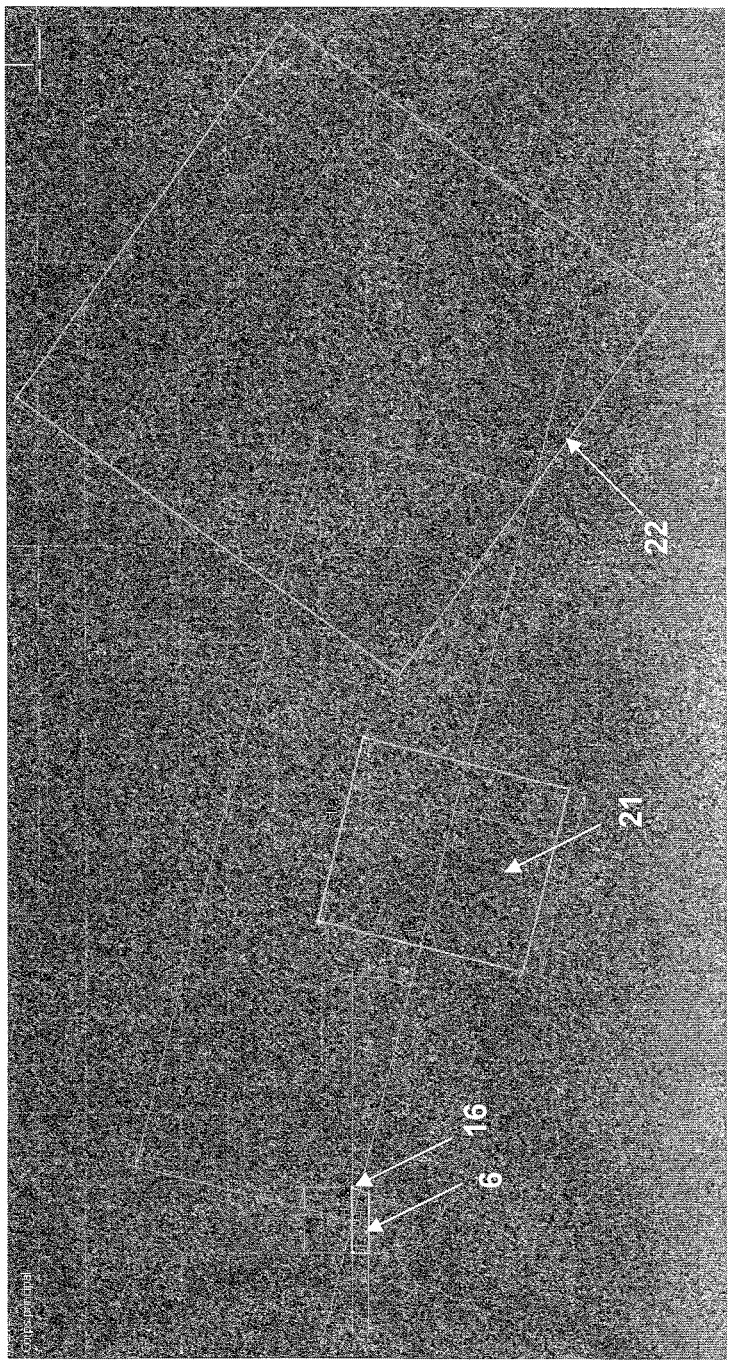
Figure 13:
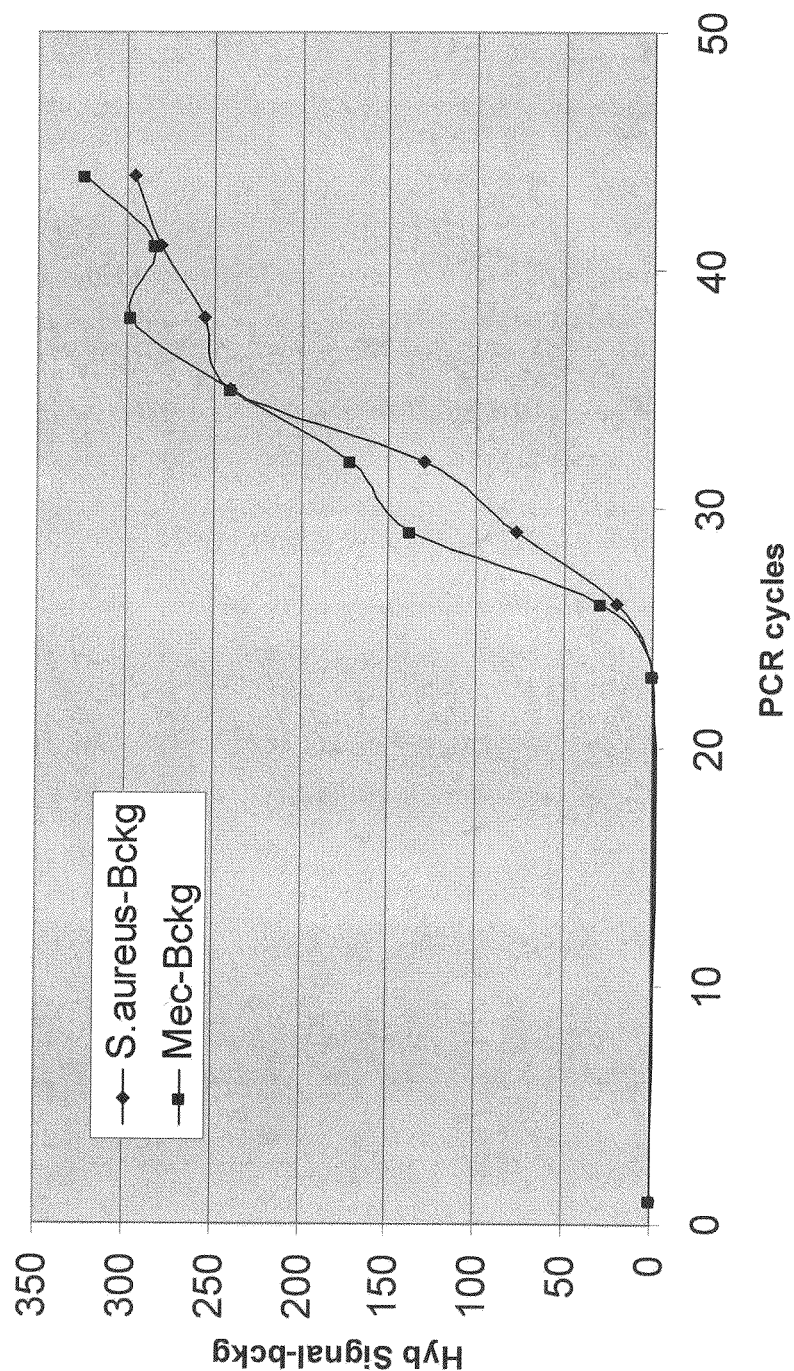

FIG. 12 represents a preferred configuration of the detection system. The optically transparent solid support (6) has an inclined side surface (16) through which the emitted light is collected. The light is concentrated by a lens (21) and focused on the detector surface (22). The captor surface (22) of the detector is tilted relative to the emitted light FIG. 13 represents the results of a real time PCR assay of two targets on an array performed in a close device having an optical part and in which the presence of amplicons is made possible at different PCR cycles by hybridization on specific capture probes and detected in the forbidden angle of the optical part of the device. The detection was done with the apparatus of FIGS. 11 and 12. The hybridizations were performed during the annealing step of the PCR and detected by taking a picture of the surface array at the end of the annealing step. The results show the appearance of the signal at the same time (PCR cycle 26) for both targets being at the same concentration. Experimental details are given in example 6.

Figure 14:
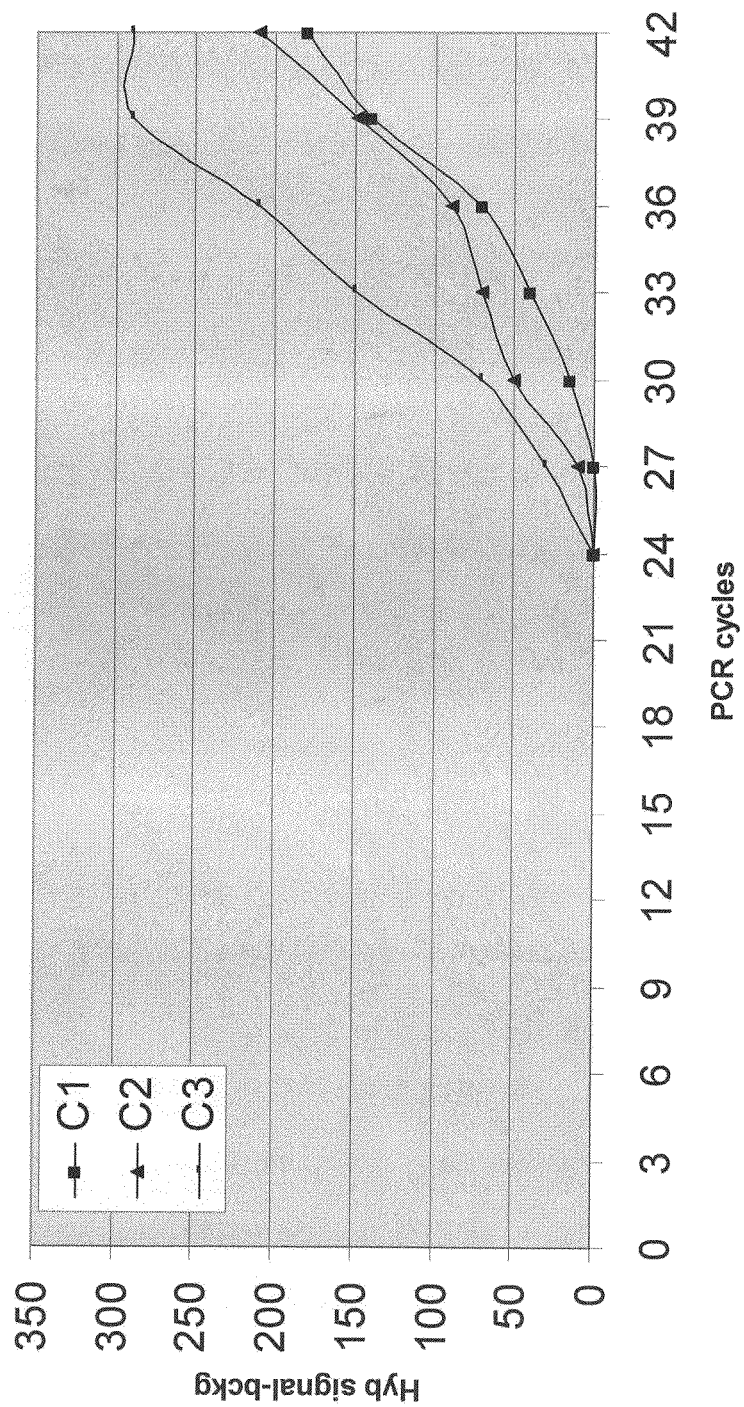

FIG. 14 represents the value for a real time PCR assay of a target at different concentrations on an array performed in a close device (as shown in FIGS. 11 and 12) having an optical part and in which the presence of amplicons is made possible at different PCR cycles by hybridization on specific capture probes and detected in the forbidden angle of the optical part of the device. The hybridizations were performed during the annealing step of the PCR and detected by taking a picture of the surface array at the end of the annealing step after shifting the liquid from one chamber to the other. The results showed the appearance of the signal at a lower PCR cycle for highest concentration of the target to be detected. Experimental details are given in example 7.

Definitions

Unless otherwise defined, all technical and scientific terms used herein have the same meaning as commonly understood by a person having ordinary skilled in the art to which this invention belongs.

The terms "nucleotide sequence, micro-array, target (and capture) nucleotide sequence, bind substantially, hybridizing specifically to, background, quantifying" are as described in WO 97/27317, which is incorporated herein by way of reference.

The terms "nucleotide triphosphate, nucleotide, primer sequence" are those described in the European patent application EP 1096024 incorporated herein by reference.

The term "gene" means fundamental physical and functional unit of heredity, which carries information from one generation to the next; a segment of DNA located in a specific site on a chromosome that encode a specific functional product. The DNA segment is composed of transcribed region and a regulatory sequence that makes transcription possible (regions preceding and following the coding DNA as well as introns between the exons).

The term "locus" means the position of the single nucleotide polymorphism (SNP) upon the sequence of the gene.

"Homologous sequences" mean nucleotide sequences having a percentage of nucleotides identical at corresponding positions which is higher than in purely random alignments. Two sequences are considered as homologous when they show between them a minimum of homology (or sequence identity) defined as the percentage of identical nucleotides found at each position compared to the total nucleotides, after the sequences have been optimally aligned taking into account additions or deletions (like gaps) in one of the two sequences to be compared. The degree of homology (or sequence identity) can vary a lot as homologous sequences may be homologous only in one part, a few parts or portions or all along their sequences. Nucleotide sequences differing by only one base are sequences highly homologous and qualified as single nucleotide polymorphisms (SNPs). The parts or portions of the sequences that are identical in both sequences are said conserved. Protein domains which present a conserved three dimensional structure are usually coded by homologous sequences and even often by a unique exon. The sequences showing a high degree of invariance in their sequences are said to be highly conserved and they present a high degree of homology.

Methods of alignment of sequences are based on local homology algorithms which have been computerised and are available as for example (but not limited to) Clustal®, (Intelligenetics, Mountain Views, Calif.), or GAP®, BESTFIT®, FASTA® and TFASTA® (Wisconsin Genetics Software Package, Genetics Computer Group Madison, Wis., USA) or Boxshade®.

The term "consensus sequence" is a sequence determined after alignment of the several homologous sequences to be considered (calculated as the base which is the most commonly found at each position in the compared, aligned, homologous sequences).

The consensus sequence represents a sort of <<average>> sequence which is as close as possible from all the compared sequences. For high homologous sequences or if the consensus sequence is long enough and the reaction conditions are not too stringent, it can bind to all the homologous sequences. This is especially useful for an amplification of homologous sequences with the same primers called, consensus primers. Experimentally, the consensus sequence calculated from the programs above can be adapted in order to obtain such property.

"Micro-arrays and arrays" mean solid supports on which single capture probes or capture probes species are immobilized in order to be able to bind given specific targets preferably protein or nucleic acid. Micro-arrays are preferentially obtained but not limited to deposition of the capture molecules on the substrate done by physical means such as pin or pin and ring touching the surface, or by release of a micro-droplet of solution by methods such as piezo or nanodispenser. Alternatively, in situ synthesis of capture molecules on the substrate is one of the invention's embodiments with light spatial resolution of the synthesis of oligonucleotides or polynucleotides in predefined locations such as provided by U.S. Pat. No. 5,744,305 and U.S. Pat. No. 6,346,413. The micro-array is preferentially composed of spots of capture probes deposited at a given location on the surface or within the solid support or on the substrate covering the solid support. However, capture probes can be present on the solid support in various forms being but not limited to spots. One particular form of application of micro-array is the presence of capture probes in wells having either one or several different capture probes per well and being part of the same support. Advantageously, micro-arrays of capture probes are also provided on different supports as long as the different supports contain specific capture probes and may be distinguished from each other in order to be able to allow a quantification of a specific target sequence. This can be achieved by using a mixture of beads having particular features and being able to be recognized from each other in order to quantify the bound molecules.

The terms "capture molecule" relate to molecules capable to specifically bind to a given polynucleotide or polypeptide or protein or to a family thereof. Preferably, polynucleotide binding is obtained through base pairing between two polynucleotides one being the immobilized capture probe or capture sequence and the other one being the target molecule (sequence) to be detected.

The term "incident angle" represents the angle between a direction incident on a surface and the line perpendicular to the surface at the point of incidence, called the normal. In the present invention, the incident angle is considered in(side) the support since the emitted light is detected going through the support.

The term "critical angle" in the present invention is the angle given in degrees in the support relative to the normal versus the solid support surface defined by $\theta_c = \sin^{-1}(n_2/n_1)$, where $n_1$ is the refractive index of the solid support and $n_2$ is the refractive index of the outside. In the present invention, $n_2$ is preferably a water solution ($n_2 \sim 1.33$) or air ($n_2 \sim 1$). The critical angle is the value of the incidence angle at which total internal reflection in the support occurs. The critical angle can be calculated and expressed in radians in the same way.

The term "observation angle" ($\theta$obin) is the angle used for the observation of the emitted light and is expressed relative to the normal in the support versus the solid support surface bearing the target molecules.

The $\theta$obout is the observation angle for the detection device located outside the support.

The "forbidden angle" of the invention is comprised between a critical angle and 90° for a light beam of a wavelength corresponding to the emitted light in the support.

The term "evanescent wave coupling" or "evanescent coupling" is a process by which electromagnetic waves are transmitted from one medium to another medium by means of the evanescent (or decaying) electromagnetic field(s).

In its common meaning, the term "evanescent field" or "evanescent wave", refers to an exponentially decaying electromagnetic field generated on the far or distal side of a totally internally reflecting interface that is illuminated by an incident light source. The evanescent wave gives an excitation energy which is the same as the energy of the wavelength of the incident light that was totally internally reflected. This energy allows the excitation of molecules fixed on the surface where the total internal reflection occurs (Induced evanescence). The evanescent field propagates with significant energy for only a relatively short distance from the distal surface of the interface (e.g., in the order of magnitude of its wavelength).

The term "emitted evanescence" or "reverse evanescence" is the reverse of induced evanescence, i.e. the process by which light emitted from objects very close (within one or few wavelengths) to the far side of a totally reflecting surface (outside the support) can be transmitted to the near side (inside the support).

The term "optical transparent" support means a support which has the features for conducting the light with a very low absorption and without bringing defects into the homogeneity of the light beam. Optically transparent means which allows at least 90% and even 95 and even 99% of the light trough the surface. Typical optical transparent support is made of high grade quality glass or material such as ZEONEX® or TOPAS®.

Fluorescent label includes fluorescent labeled nucleotides which are incorporated into the amplification product. This can either be achieved by using fluorescent labeled nucleic acid primers or labeled deoxyribonucleotides. Fluorescent label also includes intercalating fluorescent dyes like SYBR Green.

The term "real-time PCR" means a method which allows detecting and/or quantifying the presence of the amplicons during the PCR cycles. In the real-time PCR, the presence of the amplicons is detected and/or quantified in at least one of the cycles of amplification. The increase of amplicons or signal related to the amount of amplicons formed during the PCR cycles is used for the detection and/or quantification of a given nucleotide sequence in the PCR solution.

Biological target molecule means a molecule which is involved in biological processes. Target molecules are limited to nucleic acids and proteins.

DETAILED DESCRIPTION OF THE INVENTION

The inventors have found unexpectedly that the combination of two unrelated physical phenomenon: refraction between two media of different refractive index and emitted evanescence (at the emission level) solves the problem of measuring a biological binding process between targets and capture molecules at the surface of a solid support, possibly in real-time, without substantially measuring labeled target molecules present in a solution which is in contact with the surface of solid support. The present method also allows performing easily a uniform illumination of the entire array surface since there is no restriction on the direction of the illumination light for as long as it produces an excitation of the target associated label.

The main feature of the present invention is a direct and simultaneous detection and quantification of the light emitted from multiple target molecules being specifically bound to specific locations while avoiding the measurement of the light emission from the same target molecules present in the solution. Such detection of a target when binding to its specific capture molecules present in the surface location (spot) which also comprise spots for at least 2 and preferably 10 and even more preferably at least 20 different capture molecules specific of other targets being possibly present in the solution performed by taking a single image thus allowing perfect comparison of the kinetic and thus quantification with the other targets was an unexpected finding of the present invention.

The present invention provides an image of the surface of the support on which the target molecules are bound onto the surface of the detector together with the specific detection and quantification of a signal resulting from the presence of a particular target at a specific location. The image is then processed in order to attribute a signal to a specific location. Each location having a particular target is represented on the surface of the detector and associated with a specific pixel number. This pixel number represents the signal related to the amount of target bound to its specific capture molecule so as to provide its detection and quantification.

The invention allows the simultaneous detection and quantification of multiple targets being possibly present in the same solution while the assay is performed in the presence of the same targets being present in the solution.

The first advantage of the present method is the possibility to follow the binding of the targets onto their specific capture molecules with time. The time course of the binding has a lot of advantages compared to end point detection. First, there are several signals for a particular target, so that a time curve can be obtained which drastically reduce the errors compared to a single detection. Secondly, in several applications, the binding on the capture molecule could lead to a saturation signal so that the quantification is lost when several targets are present at different concentrations with end point detection. When performing real-time detection, it is possible to discriminate between the low and high target concentrations by analysis of the time curve even if both signals reach the same saturation point.

The invention opens the way to several applications not described by the prior art. When antigens have to be detected, the classical assay is to incubate a sample with the corresponding specific antibodies bound to a surface and the detection is performed after several steps of washing and labeling. This is time consuming and requires additional handling steps. The present invention allows the detection of multiple antigens while they are present in the solution so avoiding the washing steps. The method provides the technical support for homogeneous assay meaning assay in one step.

Another application is related to nucleic acid detection. One of the major technologies in molecular biology is based on the amplification of a particular nucleic acid sequence in order to be able to detect them in a specific way even in the presence of complex other genomic material. The genetic amplification step used in the invention is performed by amplification protocols well known in the art, preferably by a method selected from the group consisting of PCR, RT-PCR, LCR, CPT, NASBA, ICR, Avalanche DNA or other DNA related techniques.

In many applications, especially in diagnostic, the question is to be able to detect and/or quantify the presence of possible pathogens, mutations, genes by the detection of the presence of a particular nucleic sequence. The method is designed in order to be able to detect one or several nucleic sequences among many other ones. The method requires the possibility to amplify and to detect the appropriated sequences if present in the sample. The present invention opens the field for performing the PCR directly in the same device as the detection using end point or real-time detection during the PCR. This drastically simplifies the method, removing washing and labeling steps. The method of the invention enables the amplification together with the detection in a closed device thus eliminating the risk of contamination and allowing the automation of the process. Such a single step amplification and detection is perfectly fitted for diagnostic applications where a minimum of handling steps are required while keeping the specificity and accuracy of the assay. When PCR is used for amplification, the present invention allows real time PCR applicable to several targets being at least 4 or preferably at least 5 or even more preferably at least 10 or even 20. The possible detection of at least 5 and even at least 10 or even 20 nucleic sequences being possibly present in a sample by real time PCR was not possible before and represents a new breakthrough in the field of real time PCR. The actual real time PCR is performed in solution using specific fluorescent probes. However, each probe has to be differentiated from the other and actually the instruments only allow discriminating between 2 and sometimes 4 different probes having different fluorescent dyes. In the present invention, only one fluorescent dye is sufficient even for the many targets to detect.

In its preferred embodiment, the invention relates to a method, device and kit and an apparatus for the detection of labeled target substances bound to probes attached on a surface of a substrate said apparatus comprising an optically transparent solid support that comprises at least one target molecule bound on capture molecules present on said solid support surface (bound target molecule) and which is or is not in contact with a solution comprising target molecule (soluble target molecule), wherein refractive index of the solid support is higher than refractive index of the solution; a light source to produce a light beam of wavelength suitable for exciting the target molecule; detection system for detecting light emitted from the target molecule as a result of excitation of the target molecule, said emitted light being detected through said optically transparent solid support at an observation angle, being a forbidden angle.

The method, apparatus, device and reagent kit are preferably used for the detection and/or quantification of different target molecules being bound at different locations (spots) of a surface of an optically transparent solid support (through specific interaction with capture molecules being immobilized on the solid support surface) in presence of a medium containing the target molecules being preferably an aqueous solution. The solid support comprises at least four different capture molecules immobilized in defined locations (spots) of its surface according to a micro-array.

In the preferred embodiment, the invention provides a detection of the bound target in the presence of the solution containing such targets. In a particular embodiment, the signal to noise ratio of the light emitted from a location having bound target is at least 10 times and even better 50 times and even better 100 times higher in the assay performed within the forbidden angle compared to the signal obtained outside the forbidden angle.

In another embodiment, the solution comprising the target molecule is removed (for example centrifuged off) from the surface of the solid support, and the measurement is performed in a nano-layer of liquid and air (nitrogen gas) present above the surface of the solid support. In such case, also n1>n2.

Preferably the emitted light of the bound target through said support is the result of an emitted evanescent coupling. This may increase the signal-to-noise ratio, while still precluding any washing step. Furthermore, by centrifuging the solution back to the chamber with the array, any further step can be performed as required, allowing subsequent step determination in real-time PCR and the like. The movement in and out of the detection chamber avoiding washing the surface to analyze makes the detection possible in a close device and in multiple step analysis.

In a particular embodiment, the capture molecules are immobilized on the solid support surface of the optically transparent solid support through a layer of material being separate from the optically transparent solid support. The material may be the same or different as the material of the solid support.

The optically transparent solid support or optical block is preferably a plane parallel substrate with an inclined or oblique side surface(s) by an angle of between 90 and 60° compared to the solid support surface. The target molecules are preferably bound at different locations of the upper surface of such plane parallel substrate. The light emitted from the target molecule on the solid support surface through said inclined side surface is concentrated by a lens and focused on the detector surface. Unexpectedly, in such very simple configuration, the light emitted through said inclined surface allows imaging on the surface of the detector of the different locations having the bound target molecules simultaneously even in the presence of the same labelled targets in solution.

The angle of tilting the detector relative to the lens and the object to be imaged is preferably calculated from the Scheimpflug principle (GB Patent No. 1196, 1904). The image taken in this way is however distorted and preferably is rectified by optical or electronic means or appropriate software.

The optically transparent solid support has preferably a thickness at least equal to $d/(2 \tan(\theta obin))$, d being the length of observation area and ($\theta obin$), the observation angle (see §274 as filed). For example a thickness of 3.5 mm is required for a d being 14 mm (see new FIG. 11). The optically transparent solid support is preferably of at least 3 mm thick.

Preferably the surface opposite to the inclined side surface of the optically transparent solid support is black or covered with a colour being black or covered with colour having an absorption corresponding to the wavelength of the emitted light. The device according to the present invention has preferably a black surface opposite to the inclined surface from which the emitted light is measured. Such blackening surface would absorb more than 90% and even more than 95% and even more than 99% of the emitted light.

Blackening of this surface reduces the background detected on the detector and increases the signal to noise ratio. Preferably said black surface increases the signal to noise ratio of at least a factor of 1.2 and better of at least 1.4 and even better of at least 2 and even better of at least 5 compared to the non black surface device. Blackening the other surfaces of the optical block is an option but does not impact much the background.

Homogeneous illumination means that the excitation of the bound targets is performed with a light intensity which is identical on the surface, the variations of light illumination being lower than 50%, lower than 10% and even lower than 5% between two locations. Preferably, the variation is as defined, between any spot of an array.

Preferably, the emitted light is focused on the detector surface and is in focus for at least 4 different locations (spots) and preferably at least 8 and even more preferred 20 spots or more. The focus is such that at least some pixels of the spots are in focus and are used as detection data. The image of the surface of the solid support bearing the different locations (spots) is projected onto the detector surface, the image of the at least 4 spots and preferably at least 8 and even more preferably 20 spots or more being spatially discriminated onto the surface of the detector.

In still a further preferred embodiment, the image of the overall surface of the support having bound targets is in focus and projected at once onto the detector surface so that pixels data is attributed to the different locations having bound targets.

Preferably, the detector is a Camera or a planned detector having more than 10 pixels on which the image is projected.

The detector can be a camera either a CMOS or CCD or other form of digital sensor capable to detect different light intensity according to a spatial resolution.

In the invention, the camera is tilted compared to the lens plane (as shown in FIG. 12) in order to obtain the entire observed object in focus on the sensor plane. By tilting the camera, all spots of the array are in focus in a two dimension surface.

Preferably, the cover glass protecting the captor surface is removed. Removal of the cover glass prevented ghost image formation.

Preferably, the image is further processed to discriminate at least 4 different locations (spots) having bound different target molecules or to discriminate locations (spots) having the bound target molecules from the locations which do not have bound target molecules or surface without capture molecule. The treatment of the image allows a removal of signals which are not associated with the presence of bound targets including but not limited to dusts or durst or scratches. These defects on the surfaces emit light but more generally diffract the light and interfere with the detection of the spots if the emission is on the same surface. Such treatment reduces the background signal. Preferably, processing the image includes a subtraction of the value of the local background from the value of the location (spot). The local background for one location (spot) is the pixel value of part of the surface surrounding the said spot and not associated with another location (spot) surface.

Also preferably, the image of at least 4 different locations (spots) being spatially discriminated is simultaneously obtained onto the surface of the detector.

In a preferred embodiment, the image of at least 4 different locations (spots) being spatially discriminated is simultaneously obtained onto the surface of the detector.

Preferably, the image has at least 10 pixels and the surface corresponding to a first location (spot) has at least 1 pixel difference from a second location.

Preferably the detector is a Camera or a planned detector having at least 10 pixels on which the image is projected.

Also preferably a full image of the surface without bound targets is subtracted from the image of the surface taken during the assay of target binding thus removing the interference, defects or dusts not associate with the target presence on the surface.

Parasite light is preferably removed by baffling the light on the sides of the light path of the emitted light. Light paths either excitation and emission are protected by caches for avoiding unnecessary reflections. The optical components are preferably made of an antireflective surface in order to avoid parasite light detection.

Unwanted light is blocked from the light of interest by the use of masks restricting the light originating from the observed array locations only. These masks are preferably placed on the excitation or emission pathways to avoid the illumination of unwanted areas and to avoid reading reflections or indirect light signals, respectively. These components are preferably made thin and non reflective.

In a preferred embodiment, the refractive index of the solid support is higher than 1.33.

The observed emitted light only undergoes refraction on the external surface of the support and do not go through the support as total internal reflection, thus is not subject to the limitation linked to the total internal reflection when the support is used as a waveguide.

The present invention is especially useful when the detection of the bound targets has to be obtained in the presence of the non bound targets present in the solution or to lower the non specific signal detection due to the presence of other non related fluorescent molecules present in the solution.

In a preferred embodiment of the method and apparatus of the invention, the detection of the bound target is performed in the presence of a solution comprising the target molecule (soluble target molecule). The solution is present on the solid support for allowing the binding between the targets and the capture molecules. The solution is contained in a chamber located on the surface of the solid support having the bound capture molecules. Preferably, the chamber is fixed on the solid support. In a particular embodiment, the chamber is part of the device. In a preferred embodiment, the chamber is closed during the assay. In a particular embodiment, the chamber is made by the wall of a well. In a preferred embodiment, during the assay, the solution is moved from one section to another, thereby allowing the interaction of the solution with the bound target molecules, and allowing the bulk of the solution to be removed from the bound target molecules. Removal of the bulk of the solution stops the binding reaction and reduces the non specific diffraction of the light by dusts or scratches or solid support imperfections. As the solution is removed by for example centrifugation, a micro or nano-layer of solution remains on the surface. Single movement of the liquid in and out the optical chamber in a close device was found to be particularly useful when successful detections have to be performed as for example to follow the real time PCR on array. However, the method is not limited to measurement when the liquid is removed. Good quality images were obtained when the liquid was completely present above the substrate.

In another embodiment, the detection is performed during binding event between target and capture molecules.

In still another embodiment, the kinetic of reaction of a target on its capture molecule is followed.

Target molecules are labeled in order to be able to emit or scatter light when bound to the surface and be detected according to the present invention. The target molecules are preferably labeled with a dye selected from the group consisting of fluorescent, phosphorescent, and quantum dot.

Alternatively, the target molecules are labeled with particles or molecules or colors which scatter the illumination light, being preferably selected from the group consisting of gold particle, metallic precipitate, non-metallic precipitate or colored molecules.

Figure 1:
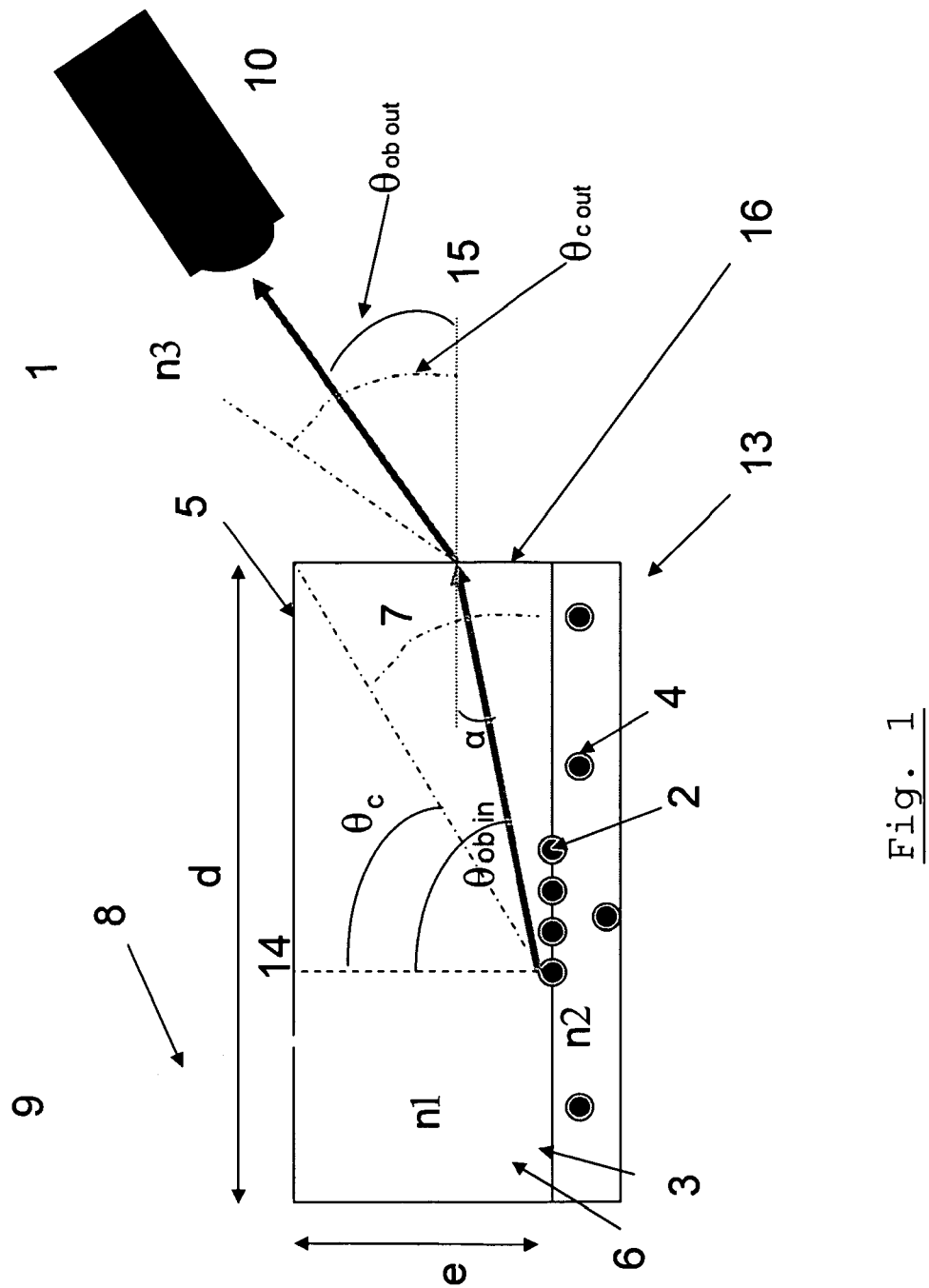
FIG. 1 gives a schematic presentation of a particular device (1) of the invention. Target molecules (2) are either bound (bound target molecule) on capture molecules present on an optically transparent inner surface (3) of the closed device or present in a solution (soluble target molecule) (4) contained in a chamber (13). The inner surface (3) is separated from outer (5) surface by an optically transparent solid support (6) having a thickness (e) suitable for detection of amplification products along an observation angle θobin inside the support comprised between the critical angle $\theta_c$ and 90°, and wherein said solid support (6) has a refractive index (n 1) higher than refractive index of aqueous solution (13) (n2). The solid support is illuminated by a light beam (8) from a light source (9). Signal from bound target molecules is measured with a CCD camera (10) located in an angle 0°<θob out<θc out measured relatively to the normal (15) of the side of the transparent solid support (16), normal to the support surface bearing the capture molecules in the support (14).

Schematic representations of some basic embodiments of the invention showing the physical principles of the process are presented in FIGS. 1 and 2 and some results in FIG. 5. In such configurations, the observation angle is such as to detect the light emitted from the bound target without much of the light from the soluble target.

In a preferred embodiment of the method and apparatus of the invention, the observation angle is higher than the value given by critical angle defined by the arcsine of the ratio between the refractive index of the medium where the capture molecule is located and the refractive index of the transparent solid support.

In another preferred embodiment, the light emitted from the bound target molecule is detected at a forbidden angle for the light emitted from the soluble target molecule.

Preferably the observation angle ($\theta_{ob}$) is within the forbidden angle range but close to the critical angle ($\theta_c$) to be able to reconstitute the image of the support. This is especially useful when different capture molecules are present on the surface of the support and have to be differentiated from each other as in the case of micro-array.

Preferably the observation angle is lower than 85° and even lower than 80° and even lower than 70°. In a preferred embodiment, the observation angle is within the forbidden angle and being in the range of the critical angle plus 10°, preferably plus 5° and more preferably plus 3°. In a particular application, the observation angle is between 62.4° and 65° when the solid support has a refractive index of around 1.5 as for glass. For glass or material having similar refractive index, the critical angle $\theta_c$ is $\sin^{-1}(1.33/1.5)=\sin^{-1}(0.887)=62.4°$. The required observation angle $\theta_{obin}$ is given by the formula $90°>\theta_{obin}>\theta_c$. In other words, the observation angle should be at least 62.4°. However as shown in FIG. 1, the $\theta_{obout}$ for the detection device could be lower than the $\theta_{obin}$.

The observation angle is lower than 90° and is not at 90° as in the Total Internal Reflection (TIR) method using the support as the wave guide. The present method is not based on the use of the Total internal Reflection in order to differentiate the emitted light from the surface from the emitted light from the solution.

In another embodiment, the observation angle is within the forbidden angle and is such that the signal coming from the solution is not significantly detected compared to the emitted light of the bound targets.

In a preferred embodiment, the light emitted from the soluble molecule does not reach the direction defined by observation angle, thus allowing the good spatial discrimination with the light emitted from the bound target molecule except for the light emitted very close to the support. The emitted light produced by the soluble molecule and detected within the forbidden angle is very small. This light contamination is a non localized signal which is deduced from the signal of the localized target. In a preferred embodiment the contamination of the signal from the localized target by the signal from the soluble target is less than 10% of the signal and even preferably less than 5% and even less than 1%.

In a preferred embodiment, the light emitted from the bound target molecule through the support is produced by emitted evanescence wave.

Supports have preferably a thickness that permit the detection of the area of interest where the targets are bound. The thickness ($e_c$) of the support is preferably greater than the value given by the formula: $e_c=d/(2 \tan \theta_c)$, with d being the length of the surface of the solid support to be detected and $\theta_c$ being the critical angle. The minimum thickness ($e_m$) for a given observation angle $\theta$ is calculated by formula: $e_m=d/(2 \tan \theta)$.

The inventors have found that in order to maintain the thickness of the support in a reasonable measure and still be able to cover a large area to be detected, it was advantageous to use a solid support having ridge channel like structure being used for observation surface. The observation area suitable to receive capture molecules are located onto the surface of a support having a ridge channel present on the opposite side of the support compared to the immobilized capture molecules. In a particular device, the ridge channels are present on second support when appropriate contact is made with the first support having the capture molecules.

Ridge channels are one example of microstructures according to the present invention. Other microstructures are possible when compatible with the detection of the emitted light as provided by the present invention. In one embodiment, microstructures are present on one of the side of the support and used as observation surface.

In a particular embodiment, a series of ridge channels are present on the other side of the support compared to the observation area having immobilized capture molecules. In another embodiment, there is one ridge channel present for one array. In another embodiment, the array is dissociated into subarrays, each of which occupies a different area on the support surface and there is a ridge channel for each of the subarrays. Subarrays mean that the array is spatially divided on the surface, each subarray being detected through the use of one ridge channel. In still another embodiment, a series of ridge channels are present on the opposite side of the support compared to the observation area having immobilized capture molecules.

Preferably the minimum thickness between the surface containing the capture molecules and the top of the ridge is given by the formula $e_m = dr/(2 \tan \theta)$ where dr is the basis of the ridge and $\theta$ is the observation angle. Preferably, the angle of the ridge ($\beta$) is equal to 90°. In a particular embodiment, the angle between the surface and the side of the ridge ($\alpha$) is equal to 25°+/−5°.

In a particular embodiment, the observation angle is the same as the surface of the ridge opposite to the observation surface. This configuration of the observation compared to the ridge minimizes the importance of the non usable images. The presence of the second surface of the ridge produces a dead observation part on the image present as dark lines and which does not contain the information on the detected targets. The preferred embodiment as explained here above allows a good detection of the observation area to be obtained.

Also, in a possible embodiment, two images of the observation area are taken at two different observation angles to reconstitute the observation area.

A particular embodiment of the device and its use for detection is presented schematically in FIG. 3. The observation surface of the ridge has to be of the highest optical quality and be preferably perfectly flat. The angle of the observation surface has to be within the forbidden angle and be constant from one channel to the other with preferably less than 1° and even less than 0.1° difference between two channels. The channels run perpendicular to the observation surface. The width of the base of each channel is adjusted from the application, the process of fabrication to be used and the resolution of the detection to be obtained. Preferably the base of the ridge is between 1 and 10 mm but can be as short as 0.1 and even 0.01 mm. Preferably, the distance between two channels is about 4 mm and the channel height is about 2 mm. The dimension of the solid support corresponds preferably to a microscopic slide (25×75 mm).

In another embodiment, the size of the ridge channels is very small with distance between the two channels being lower than 4 mm and even lower than 1 mm and even more than 0.1 mm or even lower than 0.01 mm.

In another embodiment, the ridge channel is large with distance between the two channels being larger than 4 mm and even larger than 10 and even 20 mm. The consequence of increasing the size of the ridge channel is the corresponding increase in the height of the ridge and so of the thickness of the support.

In a particular embodiment, the angle of the ridge ($\beta$) is equal to 90°. In another embodiment, the angle between the surface and the side of the ridge ($\alpha$) is equal to 25°+/−5° and the angle of the ridge ($\beta$) is equal to 90° (FIG. 3).

In the preferred configuration of the assay, the light emitted from the target in the support reach the external surface of the support with an angle of 90° plus or minus 5°. This configuration suppresses the refraction of the emitted light at the outcome of the light from the support.

In another embodiment, the angle ($\theta$obout) of the detection mean can be different from the angle of the observation inside the support ($\theta$obin) when the light emitted from the target in the support is refracted at the outcome of the light from the support as exemplified in FIG. 1. $\theta$obout is thus equal or lower than the $\theta$obin and has to be corrected for the refraction of the light coming out of the support (see example 1).

In still another preferred embodiment the observation angle is the same as the surface of the ridge opposite to the observation surface. The camera is in line with the surface of the ridge opposite to the observation one.

In another configuration, the base of the ridge has the same pitch as the spots on which are immobilized the capture molecules. FIG. 4 presents the same ridge channel structure for the observation of targets in multiple assays in a multi-well format device.

In a preferred embodiment of the method and apparatus of the invention, the surface of the solid support is maintained flat at temperature higher than 85° C. and the solid support shows a low self-fluorescence at the wavelength of excitation and emission used for the detection of the target.

In a preferred embodiment of the method and device, the optically solid support to which the capture molecules are immobilized are preferably organic or inorganic, optically transparent materials such as glass, quartz, silicon, plastics such as polycarbonate, acrylic polymers, polystyrene or cycloolefin polymer preferably ZEONEX® or ZEONOR® (Leon Chemicals, Louisville, USA), TOPAS®, UDEL®, RADEL® or THV. Still preferably the supports have a refractive index higher than water. Nonlimiting examples include the following supports with the range of refractive index higher than glass: Crown glass pure (1.50-154) or impure (1.48-1.75), Flint Glass pure (1.60-162) or impure (1.52-1.92), PMMA (1.49), PET (1.57), Polycarbonate (1.58), acrylic glass (1.49), silicon (4.01). It is preferred that n1 is about 1.40 or higher, preferably about 1.45 or higher.

In a preferred embodiment, the target is bound onto a capture molecule fixed onto a solid support at a distance lower than 500 nm and better lower than 100 nm and even lower than 50 nm so that part of the emitted light is evanescence light emitted inside the solid support.

Capture molecules are preferably bound onto the surface of the solid support or on a substrate present on the solid support in the form of an array. The binding of the capture molecules is preferably a covalent link. Methods for the binding of capture molecules are described in Zammatteo et al. (2000, Analytical Biochemistry 280, 143) given here as a non exhaustive example Capture molecules are preferably proteins or nucleic acids or nucleic acid derivative such as Peptide Nucleic Acid (PNA)

or Locked Nucleic Acid (LNA) which are able to bind to specific nucleic acids such as DNA or RNA polynucleotide sequences. Targets are also preferably protein or nucleic acids or their derivatives.

In a preferred embodiment, the biological target molecule is selected from the group consisting of nucleic acid and protein. Preferably, the protein is selected from the group consisting of antibody, antigen, ligand, and receptor.

In another embodiment, temperature control system is adapted to perform the binding or the target onto their capture molecule for example hybridization of polynucleotide sequences in the condition of salt and temperature which have to be optimized in order to obtain the specific binding of the target on their specific capture molecules with non significant binding of other non related polynucleotides.

In a preferred embodiment of the method and apparatus of the invention, temperature of the solution comprising target molecule is held constant with a variation of temperature of less than 5° C., preferably less than 1° C.

In another embodiment, temperature of the solution comprising target molecule is gradually raised or decreased according to a predetermined time pattern. For instance, the temperature may be step wise raised by 5° C. every 10 minutes to observe the dissociation of the hybridized target molecule.

Light Illumination

In a preferred embodiment of the method and apparatus of the invention, the light source produces a light beam for directing light on the surface of solid support.

In a preferred embodiment, the excitation light excites a label present on the amplified nucleotide sequences and the emitted signal is detected by a detector comprising preferably a CCD camera.

Homogeneous detection of the bound targets is critical especially when the capture molecules are immobilized on the solid support in the form of an array which occupies a certain surface on the solid support. Excitation of the bound targets should be highly uniform and/or constant whatever their position on the solid support. Homogeneous excitation is best obtained through homogeneous illumination. Homogeneous excitation can be obtained, for example, using the apparatus disclosed herein.

In a preferred embodiment, the light received by the surface of the support having fixed capture molecules at defined locations does not vary more than 10% and preferably no more than 5% within two locations.

Homogeneity of the excitation light is preferably obtained by using a diverting lens or by vibrating the light source. The illuminated surface is preferably of the same area or even greater than the surface bearing capture probes for target detection, for example 2×1 cm. The light source (preferably a laser beam) itself is also important. The intensity is preferably at least 20 mW, preferably more than 75 mW.

In a preferred embodiment, the light beam is directed on the back side reaching the support by the surface opposite to the surface having immobilized capture molecules.

In another embodiment, the light beam is directed on the front side reaching the support by the surface having the immobilized capture molecules In still a preferred embodiment, the light beam reaches the surface of the support having immobilized capture molecules with an angle of 90° plus or minus 10° and better plus or minus 5°. In a particular embodiment, the angle is outside the range of 90° plus or minus 2°.

In another embodiment, the light beam reaches the surface of the support being in contact with the external medium with an angle of 90° plus or minus 10° and better plus or minus 5°.

In another embodiment, the incident angle between the excitation light and the transparent support is equal to the Brewster angle. In this embodiment the excitation light is polarized parallel to the incident plane.

In another embodiment, the illumination is a homogeneous light which illuminates at once the entire surface of the support on which the capture molecules are hound.

In a preferred method, the excitation of the bound target is obtained by a laser beam which is focussed on the surface of the array.

In still another preferred embodiment, the scanning method is a confocal method including a pin hole.

In a preferred embodiment, the illumination light beam is smaller than the surface of the support on which the capture molecules are immobilized and the beam scans the surface.

The device for detecting a signal comprises a light source illuminating the insoluble solid support on which the capture molecules are fixed.

Preferably the scanner uses a laser beam including a confocal scanning method and also preferably a pin hole. A light source generates a beam of light to excite the labeled targets on the support.

In a preferred embodiment, the excitation light has a wavelength which corresponds to the maximum excitation wavelength of the label plus or minus 20 nm. In another embodiment, the detected light has a maximum wavelength which corresponds to the maximum of the light emitted by the label target plus or minus 20 nm.

In a particular embodiment, the method and apparatus use two wavelengths for the reading of the signal, one corresponding to the wavelength of the emitted light from the target and the other one being different by at least 10 nm and better 30 nm and even better 50 nm. The signals from the two readings are then processed in order to determine the background value and to be able to correct the specific signal from the non specific signals. This setting allows a good correction for the non specific background especially useful when working with polymeric materials.

In a particular embodiment, the method and apparatus use two or more wavelengths for the excitation and/or emission of the detected light so as to be able to detect two or more targets labeled with different fluorochromes.

In another embodiment of the method and apparatus of the invention, the light source produces evanescence excitation of the surface of solid support.

In a preferred embodiment the surface of the support is fixed relative to the light beam. In another embodiment, the support moves relative to the light beam or to the light source.

The light source is preferably a laser that generates a beam having a wavelength of about 532 nm delivered at a power of about 15 mW with a divergence that may be below 1.2 mrad. In another embodiment, the light source is preferably a laser that generates a beam having a wavelength comprised between 639 and 659 nm. In another embodiment, the light source is preferably a laser that generates a beam having a wavelength comprised between 733 and 753 nm.

The laser beam generated by laser is preferably nearly collimated and nearly Gaussian. An exchangeable excitation filter is preferably used to collect only the wavelengths of interest. An additional filter wheel is placed and be used as an attenuation filter to regulate precisely the laser power. This filter wheel may be shaded differently at variable known absorption levels. A lens that is anti-reflection coated is preferably used for focusing the laser beam on the micro-array. The distance between the light source, the lens and the support is variable to allow focusing. Thereafter, the light passes through a dichroic mirror. This mirror preferably passes light having a wavelength of the excitation light but reflect light having a wavelength greater than the emitted light. Consequently, the light coming from the laser is passed through the dichroic mirror to the support. The light then passes through third chamber and reaches the surface of the support, where bound labeled target molecules are excited and emit fluorescence. Emitted fluorescence is transmitted through an emission filter chosen for letting pass wavelength greater than the emission light. Preferably the emitted light goes through an objective for magnification of the image sample. The fluoresced light is then focused to a photomultiplier tube for detecting the number of photons present therein. In a specific embodiment, an additional emission filter that transmits light having a wavelength greater than the emission light is added. Thus, photomultiplier tube detects substantially only fluoresced light. The Photomultiplier tube generates a pulse for each photon detected. Each of these pulses is amplified and converted to an electronic signal by photoelectric effect. A data acquisition board then collects the resulting signals.

The light source is preferably a collimated punctual light or a linear homogeneous light. In a preferred embodiment, the light source is obtained from gas lasers such as argon laser.

Preferably, the linear source is obtained by using an optical fiber bundles as proposed by Aurora Photonics Inc. (26791 West Lakeview, Lake Barrington, USA; www-auroraphotonics.com) and as disclosed in U.S. Pat. No. 6,620,623 (which is hereby incorporated by reference herein). The collimated laser source is preferably a low power collimated laser diode or a light emitting diode (LED). Preferably, the power ranges between about 1 mW and about 25 mW. The collimated laser diode emits at a specific wavelength, preferably between about 470 nm and about 650 nm. Alternatively, a LED coupled with optical filter can also be used as an illumination source. A fiber optic bundle directs the light to the surface of the support having immobilized capture molecules or on the backside of a glass substrate. The light is directed to the backside of the glass substrate by the fiber optic bundle that is formed preferentially but not limited by borosilicate fiber light guides, quartz fiber light guides or plastic fiber light guides or fiber light guides formed by another suitable material. The fiber optic bundle is carried by a positioner and is splayed out to make a respective fiber optic fan. The fiber optic fan is one fiber thick, each defining a light line or linear array of a plurality of optical fibers. The fiber optic bundle includes a plurality of optical fibers providing generally symmetrical illumination of the glass substrate.

In another embodiment, the light produced by said optical fibers is guided through multiple total internal reflexions inside the transparent support. As described above, the transparent support and the medium where the probes are located follow the total internal reflection conditions in terms of refractive index. In these conditions, an evanescent field exists at the surface of the transparent medium. The penetration depth of the evanescent field is in the same order as the wavelength, about a few hundreds of nanometers for visible fluorescence. As the labeled targets bound to the attached probes on the transparent support are comprised within the same order, this results in selective excitation of the bound labeled target (induced evanescence) while the soluble labeled target located at a greater distance than the penetration depth of the evanescent field are not excited, thus the amount of background brought by the soluble labeled targets is negligible.

In another embodiment, the linear light is obtained by defocusing a collimated light using a divergent lens illuminating a thin slit focused on the surface of the support.

Detection

In a preferred embodiment, the device is fixed during the signal detection and the optical system moves relative to the device to scan the micro-array.

In another embodiment, the incident light source, the device and the detector are not moving relative to each other. In this embodiment, the detection method is preferably a CCD camera having a matrix CCD sensor and collecting the light of emitted from the target in a single acquisition. Example of such sensor is the Retiga 4000R Fast 1394 Mono Cooled (QImaging, Surrey, Canada). The cooling of the CCD removes the dark current noise and enhances the system sensitivity. A lens mounted on this camera allows the real-time monitoring of the binding of the target. In a preferred embodiment, a pass-band filter allowing emission wavelengths only reduces the noise coming from the excitation light.

In a preferred embodiment, the Fluorescence emission is collected by a CCD camera preferably with peltier cooling (−18° C.) which contains a CCD chip with 765×512 pixels. The dimensions of a pixel are 9 μm×9 μm and the overall size of the CCD sensor is 6.8×4.6 mm. To obtain maximum image resolution, the array is situated as close as possible to the lens. To image a sensing area of 14×14 mm² of the array onto the CCD chip, the magnification has to be set to g=1/3.2 (~4.6/14 mm). This can be achieved by using a 5 mm extension tube, which made it possible to position the camera lens at a distance of 75 mm from the array.

In the preferred embodiment where the CCD is placed in said angle wherein only the light emitted from the bound labelled target can be observed, the distortion of the image seen through the lens can be corrected in several manners. One embodiment is to apply a one-dimensional numerical stretch on the image using any image processing software i.e. Photoshop CS2 (Adobe Systems Inc., San Jose, USA). Another preferred embodiment is to rotate the CCD sensor with an angle equal to the observation angle but in the other direction given the presence of a lens in the optical path. This optical treatment does not alter the image at the opposite of the numerical processing described above. This particular setting of the instrument is a preferred embodiment since it allows a complete focussed image of the array to be obtained at once. Image deformation is then corrected by software rectification in order to obtain the geometry corresponding to the original array.

In an alternative embodiment, the array is scanned row for row (and not spot by spot), by applying homogeneous illumination and a camera that is able to measure one row at a time in-focus. This hybrid between spot-by-spot scanning and a complete picture has the advantage that scanning is substantially faster than spot-by-spot scanning, allowing a better comparability between the spots, and yet requiring less limitations in the camera set-up.

In another embodiment, the device moves relative to the optical system to scan the micro-array.

After data are collected from a region of the micro-array, the device moves so that light can be directed at a different discrete region of the micro-array. The process is repeated until all discrete regions of the micro-array have been scanned.

In still another embodiment, the resolution of the optical system is between 0.1 microns and 500 microns and more preferably between 10 and 100 microns.

In a particular embodiment, the device comprises or is made of a material selected from the group consisting of glass, polymer, or a mixture thereof. The polymer is preferably selected from the group consisting of: polycarbonate (PC), polyethylene (PE), cycloolefin copolymer (COC), cyclicolefin polymer (COP) and a mixture thereof. In a specific embodiment, cycloolefin polymer is preferably ZEONEX® 330R or ZEONOR® (Zeon Chemicals, Louisville, USA), Topas®, Udel®, Radek® or THV.

In a particular embodiment, the transparent support is in contact with a prism and the detection system is placed close to one other side of the prism as shown in FIG. 2. The optical contact between the prism and the transparent support is made using a liquid or gel having a refractive index close to the refractive index of said prism and transparent supports. In the embodiment described above the refractive index for the Zeonex is equal to 1.51, the prism made of glass having a refractive index of 1.50, said liquid can be for example glycerol (refractive index equal to 1.47).

In a particular embodiment, the device comprises the following parts: a transparent Zeonex slide (500 µm thick) having a surface on which the probes are bound. This part is preferably functionalized to facilitate the binding of said probes. This part is sealed with a second part; said second part is made of black Zeonex plastic and is thin to allow good thermal transfer between the heating element directly in contact with this second part. This second part further comprises two injection holes allowing to inject the sample containing the soluble labelled targets inside the chamber fanned by the empty space between said two parts. Said injection holes are tightly sealed after injection of the sample by for example aluminium foil or other adhesive temperature resistant or by using an integrated plug that can be clipped inside said injection hole, the tightness being ensured by an o-ring made of elastomer mounted on said plug.

The chamber formed by said two parts has preferably a volume of 100 µl. The dimension of the hybridization chamber formed by the empty space between said two parts is preferably 2×2 cm and 330 µm thick.

The optical system for the detection comprises the following parts:
  a light source that can be a laser or a diode as described above
  optical elements that can be one or more lenses, excitation filter, emission filter, polarizer, slit to generate the desired lightning system as describe above
  a computer storage system records the intensity of the light measured by the sensor and stores it as a function of the location of the excitation.
  a translator system moving all the optical system and exciting another location on the surface of the transparent support, leading to a different intensity measured by the sensor corresponding to a different location
  a software driving the entire system and repeating all of the steps of measurement at another location of the transparent support. The result is a function of the intensity corresponding to the location on the surface of the support and allows to produce a two dimensional image of the labelled target bound to the probes on the surface.

In a preferred embodiment, the detection of the bound target is performed in the presence of a solution comprising the target molecule (soluble target molecule) said solution being contained in a closed chamber.

In a preferred embodiment, the apparatus further comprises a heating element capable of changing temperature of said solution, thereby enabling binding reaction between target and capture molecules. Preferably, the heating element adapts the temperature of the solution to maximize the binding between to said target substances and said probes.

In another embodiment, the heating element is capable of cycling a temperature of said solution, thereby enabling amplification reaction.

The temperature control system may be a controlled peltier element, a micro-thin wire heating element laid in a pattern between optical grade polyester sheets like Thermal-Clear™ transparent heaters from Minco, or fluidic system circulating externally temperature regulated fluid. The temperature control system is composed of an active temperature control system and a temperature control unit, allowing to regulate precisely the temperature and to perform temperature cycles. Software In a preferred embodiment, said two-dimensional reconstructed image is analyzed using a micro-array image analysis package such as Image 7.0 (Biodiscovery, El Segundo, Calif., USA) or Genepix 6.0 (Molecular Device, Sunnyvale, Calif., USA). Pixels corresponding to bound targets have a higher intensity than pixels corresponding to the background of the slide. These pixels are identified automatically by the image analysis software and linked to the target information respective to the location. A mean of the intensity of all pixels is computed and given as output.

In a preferred embodiment, each image corresponding to a different acquisition in the time is quantified, and the signals for each target are analyzed using the time parameter.

In another embodiment, the time results for each target are used to generate kinetics data.

In a preferred embodiment, each image is analyzed immediately after acquisition.

Probes and Detection Methods

The label-associated detection methods are numerous. Detectable labels suitable for use in the present invention include any composition detectable by electromagnetic light emission. A review of the different labelling molecules is given in WO 97/27317, which is hereby incorporated by reference herein in its entirety. They are obtained using either already labelled primer, or by enzymatic incorporation of labelled nucleotides during the copy or amplification step or by chemical reaction on fluorochrome or by intercalating agents followed by fluorescent detection (WO 97/27329, which is hereby incorporated by reference herein in its entirety). Fluorochromes can be incorporated into the targets by chemical reaction such as the reaction of fluorescent dye bearing a N-hydroxysuccinimide (NHS) group with amines groups of the targets. Useful fluorescent dyes in the present invention include cyanine dyes (Cy3, Cy5, Cy7), fluorescein, texas red, rhodamine, green fluorescent protein or Alexa dyes (Invitrogen, Carlsbad, Calif. USA), Oyster (DeNovo Biolabels GmbH, Heideleberg, Germany).

The preferred labels are fluorochromes which are detected with high sensitivity with fluorescent detector. Fluorochromes include but are not limited to cyanin dyes (Cy3, Cy5 and Cy7) suitable for analyzing arrays by using commercially available array scanners (as available from, for example, General Scanning, Genetic Microsystem). Preferably, the excitation wavelength tbr cyanin 3 is comprised between 540 and 558 nm with a maximum at 550 nm, and the emission wavelength is comprised between 562 and 580 nm with a maximum at 570 nm.

Preferably, the excitation wavelength for cyanin 5 is comprised between 639 and 659 nm with a maximum at 649 nm, and the emission wavelength is comprised between 665 and 685 nm with a maximum at 670 nm. Preferably, the excitation wavelength for cyanin 7 is comprised between 733 and 753 nm with a maximum at 743 nm, and the emission wavelength is comprised between 757 and 777 nm with a maximum at 767 nm.

In a preferred embodiment, the fluorochromes are chosen in order to react to excitation wavelength being higher than 600 nm and even higher than 650 and even higher than 700 nm. High wavelength of excitation and emission reduces the intrinsic fluorescent background of most of the polymer materials which are used preferably as solid supports.

In a preferred embodiment, the excitation of the fluorophore molecule is obtained preferably on the fluorophore present on target bound to the capture molecule rather that on the fluorophore present in the solution preferably by a laser beam which is focussed on the surface of the array.

In a preferred embodiment, the target molecule is labelled with a dye selected from the group consisting of fluorescent, phosphorescent, quantum dot.

The inventors found that the fluorescent background and scattering originating from the support material defects and dusts are reduced when dyes with a large Stokes shift are used. In a preferred embodiment the Stokes shift of the dye is at least 20 nm, at least 30 nm and better 50 nm and even better at least 80 nm and even better at least 100 nm between maximum excitation and emission wavelength. Assays were made with fluorescent dye LSS 520 polynucleotides from Promokine (Heidelberg, Germany) having a absorption maximum at 520 nm and an emission maximum at 664 nm. Results indeed showed a reduction in the background but also in the scattered light produced by the impurities and imperfections or defects on the surface of the optical support. Other dyes with Large Stokes Shift (LSS) are available from the same company having different absorption maximum ranging from 485 to 520 nm and emission maximum ranging from 560 to 664 nm. The choice of the dye will be related to the detection instrument, mainly the production of the excitation light preferably with a laser and by the type and features of the detector of the emitted light. In a preferred embodiment, the Stokes shift dye leads to a signal to noise ratio of at least 2 and better at least 5 and even better at least 10. Dyes with large Stokes shift are commercially available or have been described for example in US Application publication number 20080206886, U.S. Pat. Nos. 4,520,110, 4,542,104, 5,326, 692 and 6,335,440. Other interesting dyes are KODAK X-SIGHT Large Stokes Shift Dyes available from Carestream Molecular Imaging (Rochester N.Y. USA). They have a large separation (80-90 nm) of absorption and emission. Dye Kodak X-Sight 640 is the preferred one having a excitation maximum of 635 nm and a Stoke shift of 98 nm.

In a particular embodiment the fluorescent dye shows an anti-Stokes type of radiation having Fluorescence radiation occurring at shorter wavelengths than absorption PAC, 1984, 56, 231 (Nomenclature, symbols, units and their usage in spectrochemical analysis-Part VI: molecular luminescence spectroscopy) on page 236.

Also in a particular embodiment the fluorescence is emitted by energy transfer from one dye to the other in a physical process known as fluorescence resonance energy transfer (FRET) which also allows to obtain a large separation between the maximum of excitation and emission wavelength.

In another embodiment, the target molecule is labeled with particles or molecules which scatter the illumination light being preferably selected from the group consisting of gold particle, metallic precipitate, non-metallic precipitate. The emitted light is the results of a scattered light emission.

In a preferred embodiment, the target molecule is labeled with gold particles. Gold nanoparticules are currently available and they can be easily fixed to molecules like protein. For example, anti-biotin antibody coated gold particles or streptavidin coated gold particles are available on the market.

According to a preferred embodiment of this invention, one uses a labeled target molecule, which is then recognised by a conjugate. This labeled molecule (biotin, haptens, etc.) can be considered as a first member of the binding pair. For DNA, the labeling is easily done by incorporation of biotinylated nucleotides during their amplification. For the RNA, biotinylated nucleotides are used for their copy in cDNA or thereafter in the amplification step. Amplification of the nucleotide sequences is a common practice since the target molecules are often present in very low concentrations. Proteins are easily labeled using NHS-biotin or other reactions. Once the biotinylated molecules are captured, an anti-biotin antibody (or streptavidin) gold complex, which is the second member of the binding pair, is added and the antibody (or streptavidin) recognizes biotin, so that the complex is fixed at the location where the target is bound.

Advantageously, gold particles catalyze a chemical reduction of silver ion (Ag+) into metallic silver (Ag) which precipitates at the location of target molecules bound upon micro-array as proposed in WO 00/72018. Advantageously, a reduction of silver in the presence of colloidal gold allows the formation of a precipitate at a distance not exceeding few micrometers from the target molecule bound to its capture molecule. The precipitate has the form of small crystals that reach with time a diameter of about 1 μm. The formation of these small crystals represents a real amplification of the signal since they originated from the presence of gold particles a few run in diameter.

The conventional procedure is that, a certain time after the beginning of the reaction which leads to a metallic precipitation on the array elements on which the interaction between target and capture molecules has occurred, a picture or image is taken and concentrations are assigned to the measured grey values, which depend on the degree of precipitation. However, this procedure only leads to satisfactory values for each array element in a quite narrow concentration range. The reason for this is that the formation of the precipitate is highly non-linear. In particular, the time course of the precipitation includes an exponential rise with time, followed by a saturation plateau. Only grey values from the phase of exponential increase allow a correlation with the quantity of bound target. The saturation plateau for the array element is dependent on the target concentration and is therefore reached at a different time for each element of the array.

In order to increase the dynamic range of the precipitation reaction, it is possible perform a time course of the formation of the precipitate. The method, apparatus, device and kit of the invention are particularly well adapted to the detection of the precipitate formation as provided in example 4.

In a preferred embodiment, the kinetics of catalytic reduction of a metal in presence of gold particle is followed.

In another embodiment, the kinetics of catalytic reaction of an enzyme in presence a substrate is followed. The detection may be performed in colorimetry or chemiluminescence according to the substrate used.

Some fluorescent labels may be of particular interest, such as nanocrystalline particles having fluorescent properties. The most common ones are the Quantum dots (Han et al. 2001, Nature Biotechnology, 19, 631). They are fluorescent and do not bleach with time or with illumination. Their stability makes them particularly suitable for the use in continuous reading, as proposed in this invention. Also, they contain metals that confer to these particles specific properties, so that other methods than fluorescence can be used to monitor their attachment to the capture molecules. Thermal heating of these particles is one of the parameters that may be monitored with time. The fact that the metal absorbs the energy of a light beam, preferably a laser beam, and induces heating of the particle, has been used as a basis for the detection of low density gold particles on a support, and even single particles are detected (Boyer et al., 2002, Science, 297, 1160). The method is called Photothermal Interference contrast.

In a particular embodiment the bound molecule hybridized on the capture molecule as a DNA double helix shows a difference in the anisotropy, compared to the free moving molecule in solution. The anisotropy depends on the mobility and the lifetime of the fluorochromes to the detected.

In a particular embodiment, the detection of fluorophore molecule also includes a time-resolved process. Fluorescent molecules have a fluorescent lifetime associated with the emission process. Typically lifetimes for small fluorophore such as fluorescein and rhodamine are in the 2-10 nanosecond range. Time-resolved fluorescence (TRF) assays use a long-lived (>1000 nanosec) fluorophores to discriminate assay signal from short-lived interference such as autofluorescence of the matrix or fluorescent samples which have shorter lifetimes less than 10 ns. Lifetime is preferably modulated by the presence in the vicinity of another fluorophore or a quencher with which a resonant energy transfer occurs. Instruments for TRF simply delay the measurement of the emission until after the short-lived fluorescence has died out and the long-lived reporter fluorescence still persists. Fluorescence lifetime can be determined in two fundamental ways. The time domain technique uses very short pulses (picosecond) of excitation and then monitors the emission in real-time over the nanosecond lifetime. Fitting the decay curve to an exponential yields the lifetime. The frequency domain technique modulates the excitation at megahertz frequencies and then watches the emission intensity fluctuate in response. The phase delay and amplitude modulation can then be used to determine lifetime.

In a particular embodiment, the fluorescent signal of the amplicons in solution is quenched and is lower compared to the hybridized target. A primer is labeled with a fluorochrome which is fluorescent when free in the solution and is quenched when incorporated into the amplicons. The fluorescence quenching is preferably obtained by using a quencher such but not limited to Dabcyl incorporated in the second non fluorescent amplicon strand. One specific embodiment used the Plexor™ Technology (Promega). This technology takes advantage of the highly specific interaction between two modified nucleotides: isoguanine (iso-dG) and 5'-methyliso-cytosine (iso-dC). In the real-time PCR reaction, one primer is synthesized with an iso-dC residue and a fluorochrome at the 5' end. The second primer is unlabelled. Iso-dGTP nucleotides, modified to include Dabcyl as a quencher, are included in the reaction mix. During the amplification only Dabcyl-iso-dGTP is incorporated at the position complementary to the iso-dC residue and as a result of the close proximity between the two residues, the fluorescence is quenched. The hybridization of the one amplicon strand carrying the fluorochrome on the capture molecule would restore the fluorescence emission.

In an alternative embodiment, the lower signal of the amplicons in solution is obtained by a difference in the optimal wavelength of fluorescence excitation between the amplicons present in solution and immobilized on the capture molecule. In still another embodiment, the lower signal of the amplicons in solution is obtained by a difference in the optimal wavelength of fluorescence emission between the amplicons present in solution and immobilized on the capture molecule.

Preferably, the difference in the wavelength of fluorescence emission is obtained by fluorescence resonance energy transfer (FRET). In one specific embodiment, a primer is labelled with a fluorochrome (F1) having a given optimal fluorescent emission wavelength and serving as donor which is fluorescent when excited at its excitation wavelength in the solution. The incorporation of the primer into the amplicon at proximity of a fluorochrome acceptor (F2) would result in an optimal fluorescence emission wavelength different from the fluorochrome F1. By detecting the fluorescence emission at the wavelength corresponding to the optimal emission of F1, the signal will be optimal for the hybridized amplicons and will be lower for the amplicons present in the solution. Particularly, the primer is synthesized with an iso-dC residue and a fluorochrome donor (i.e. TAMRA) at the 5' end and the solution contains Iso-dGTP nucleotides, modified to include a fluorochrome acceptor (i.e. Cy5). During the PCR, the amplicons are formed with the two fluorochromes being at close proximity as explained previously for the Plexor™ Technology (Promega). Detection is then performed using an excitation/emission wavelength optimal for the donor. As a result of the close proximity between the donor and the acceptor, the detected fluorescence is decreased in solution. The hybridization of the amplicon strand carrying the donor on the capture molecule would restore the optimal fluorescence emission.

Array

The detection of the target molecules are performed on immobilized capture molecules. The capture molecules are preferably immobilized in the form of micro-array.

In a preferred embodiment, between 1 and 1000 target molecules, preferably between 1 and 100 target molecules, more preferably between 1 and 20 target molecules present in solution are detected and/or quantified in the same assay.

In a preferred embodiment of the method and apparatus of the invention, the solid support comprises multiple capture molecules immobilized in defined locations of its surface according to a micro-array.

In another embodiment, the micro-array comprises more than 5 different capture molecules, preferably more than 20 and even more than 50.

In another preferred embodiment, wherein the surface of emission of a defined location is comprised between 1 µm² and 1 mm².

On the micro-array, capture probes are arranged at defined and/or pre-determined locations at a density of at least 4, 10, 16, 20, 50, 100, 1000, 4000, 10 000 or more, different capture probes/cm² insoluble solid support surface. The capture probes are advantageously covalently attached to the surface of the solid support (preferably a non porous solid support surface) by one of their extremities, preferably by their 5' end. The sensitivity may be further increased by spotting capture probes on the solid support surface by a robot at high density according to a micro-array. The amount of capture probes spotted on the micro-array is preferably comprised between about 0.01 to about 5 picomoles of sequence equivalent/cm² of solid support surface.

The capture molecules are preferably polynucleotides or proteins. Preferably, the spots of the array are spatially distant in a two dimensional pattern. Preferably the spots are arranged in the form of an array of at least 4 and preferably at least 15, and even more preferably at least 20 and even more preferably at least 50 spots having immobilized capture molecules. Even more preferably, the spots are in a regular pattern, for example as 2×2, 2×3, 2×4, 2×5 or 2×10; 3×3, 3×4, 3×5, 3×8, 3×10, 4×5, 4×10, 5×8, 10×10 and the like. Generally, the number of spots is about 500 or less, and—for practical reasons—about 100 or less. Preferably the pattern of the spot distribution in two dimensions on the surface has a geometrical form one being a square or a rectangle.

In one embodiment, the molecules are polynucleotide sequences which capture portion is preferably comprised between about 10 and about 1000 bases, preferably between about 15 and about 100 bases and more preferably between 18 and 30 bases. These bases are preferably assigned as a continuous sequence located at or near the extremity of the capture probes (nucleotide sequences). This sequence is considered as a specific sequence for the detection of the target nucleotide sequence.

In another embodiment, the capture molecules comprise polynucleotide sequence having a specific capture portion of 10 to 100 nucleotides that is complementary to the specific target sequence to be detected and a spacer portion (linker).

In a preferred embodiment, the capture polynucleotide sequence comprises:
- a capture portion of 10 to 100 nucleotides that is complementary to a specific sequence of the target amplicons such that said capture portion define two non-complementary ends of the amplicons and
- a spacer portion having at least 20 nucleotides, and wherein the two non-complementary ends of the amplicons comprise a spacer end and a non-spacer end, respectively, such that the spacer end is non-complementary to the spacer portion of the capture nucleotide sequence, and said spacer end exceeds said non-spacer end by at least 50 bases.

In a preferred embodiment, the spacer portion is a polynucleotide being at least about 20 nucleotides long, at least about 40 or about 70 nucleotides and preferably at least about 90 nucleotides long. The spacer portion is a given nucleotide sequence being homologous to none of the genome sequence (when using an identity of at least 10 and better 5 consecutive bases). To avoid non specific hybridization, there will be no more than around 15 consecutive complementary base pair bindings between a target polynucleotide (or nucleotide) sequence and the spacer portion, preferably there will be less than 10 such pairings possible, more preferably less than 5. As such, the nucleotide sequence of the spacer portion will contain, preferably less than 15 bases and more preferably, less than 10 and still more preferably less than 5 contiguous bases complementary to the target nucleotide sequences to be detected. The determination of possible consecutive sequences is easily done by comparison of the sequences to molecular database as provided by Genbank and using software such as nucleotide-nucleotide BLAST (blastn) (www-ncbi.nlm.nih.gov/BLAST).

The spacer portion is preferably located at the 5' extremity of the capture nucleotide sequence being fixed to the surface of the solid support by a covalent link present at the 5' end or nearby. The capture portion is preferably located at 3' end of the capture nucleotide sequence (free extremity not bound to the support) at 1 to 23 nucleotides from the end.

The length of the capture molecules for polynucleotide detection has to be optimized and designed according to the application, the required specificity and the sensitivity of the assay. The total length of the capture probes (nucleotide sequences) including the possible presence of a spacer portion is comprised between about 30 and about 800 bases, preferably between about 35 and about 200 bases, more preferably between about 39 and about 120 bases.

In another preferred embodiment of the invention, capture probes (nucleotide sequences) are chemically synthesized oligonucleotide sequences of about 100 bases, which may e.g. be easily performed on programmed automatic synthesizer. Such sequences can bear a functionalized group for covalent attachment upon the support, at high concentrations. Longer capture nucleotide sequences are preferably synthesised by PCR amplification of a sequence incorporated into a plasmid containing the capture portion of the capture nucleotide sequence and spacer portion.

Applications

In a preferred embodiment, the present invention is used for identification and quantification of an organism by the detection of part of its genome. Also the present invention is useful for the detection of the expressed genes of an organism or cells or tissues. The expressed genes are present in the form of mRNA which is then copied into cDNA and used as target for amplification or direct detection on capture molecules such as on array. Also the genome of the organism can be checked for the presence of mutations (Single Nucleotide Polymorphism or SNP) or deletions.

The genetic amplification step used in the device of invention is performed by amplification protocols well known in the art, preferably by a method selected from the group consisting of PCR, RT-PCR, LCR, CPT, NASBA, ICR or Avalanche DNA techniques.

In a preferred embodiment of the method and apparatus of the invention, the solution comprising target molecule is submitted to temperature cycles having at least 2 and preferably 3 different temperatures. Preferably, the temperature cycles are those which produce a PCR.

In a preferred embodiment, the reading of the signal is performed in presence of solution containing the amplified nucleotide sequences. In another embodiment, the reading of the signal is performed in absence of the solution containing the amplified nucleotide sequences.

In another particular embodiment, the method is used for measuring the binding kinetics of a particular target onto the capture molecule. In this embodiment a rate constant is calculated from the at least 2 data obtained at 2 different times of incubation. In a particular embodiment the rate constant is used for the quantification of the target present in the solution.

In a particular embodiment, the present method of the invention further comprises the step of calculating the binding constant of the target to its capture molecule. The method is especially useful to evaluate the binding constant of a particular antibody or of a ligand towards its receptor.

The method of the invention is particularly adapted for performing multiple assays in parallel and preferably is compatible with the multi-well format.

In the method and device of the invention, several separated observation areas are processed at one time. Preferably, the observation area is composed of surfaces distant from each other of pitch compatible with the distance of the 24, 96, 384 or even 1536 wells in the multi-well format. Preferably the observation area is distant from each other by 18, 9, 4.5 or even 2.25 mm. In a preferred embodiment, a series of ridge channels are present on the opposite side of the support compared to the observation area having immobilized capture molecules.

In another embodiment, the observation area suitable to receive capture molecules is located onto a ridge channel present on the opposite side of the support compared to the immobilized capture molecules. Examples of such embodiments are presented schematically in FIGS. 3 and 4.

Organism Identification

One preferred application is the detection of an organism or part of it in a sample potentially containing at least four nucleotide sequences from other organisms said process comprising the step of: amplifying DNA from said organism or part of it into double-stranded target polynucleotide sequences by at least two PCR cycles using one or multiple primer pairs which are capable of amplifying at least a DNA sequence from said 5 organism; contacting said target nucleotide sequences with a single-stranded capture molecule, said single-stranded capture molecule being covalently bound in a location of an array to an insoluble solid support, and wherein said capture molecule comprises a capture portion of between 10 and 600 bases able to specifically bind to said target nucleotide sequence without binding to said nucleotide sequences from the other 4 organisms; and detecting specific hybridization of the said target nucleotide sequence to the said capture molecule.

SNP

The device of the invention is particularly adapted for the identification of multiple single nucleotide polymorphisms or multiple mutations (multiple SNPs) present at different gene loci. Preferably, said detection or characterization is obtained upon the same micro-array.

In preferred embodiment, the nucleotide sequence to be detected in the device is a nucleotide base or SNP. In the first step, the nucleotide sequence of a gene is amplified using at least one primer pair (i.e. a pair of two different primers). However, several primer pairs are either used for amplifying the different specific nucleotide sequences of a gene, these sequences being preferably different exons, or used for amplifying different genes or different parts of a cell genome.

Preferably, each amplified target sequence comprises several loci. All these loci of the target are then amplified with the same primer pair being consensus primers for an amplification of all these loci, but each locus is detected on specific capture probes.

Therefore, the micro-array contains capture probes specific for one or more loci for hybridization with target nucleotide sequence(s) comprising the SNP to be detected in each locus, the different mutated bases being located in the same exon or in different exons originating from the same gene or from different genes, preferably present in the same nucleotide sequence. The amplification step of these several exons is preferably obtained with different primer pairs, each primer pair being specific for one exon. Amplification of several exons is preferably performed in the same conditions for all exons in the PCR chamber 1.

Parts (or portions) of the gene or genome sequence (loci) having possible mutations to be detected can be firstly amplified by PCR and the resulting amplicons are fragmented by DNAse treatment in chamber 4 (Grimm et al. 2004, Journal of Clinical Microbioloy, 42, 3766-3774). In the preferred embodiment, the resulting amplicon fragments are between 30 and 70 bases long. The distribution of the fragments size obtained after fragmentation of the amplicons is advantageously checked by analysis by capillary electrophoresis (Bioanalyser, Agilent) and the average size distribution of the pieces is preferably comprised between 30 and 70 bases long.

The capture probes preferably differ by one base (SNP) located at 4 to 10 and preferably at 4 to 6 bases from the (free) 3' end of the target specific part (portion) of the bound capture probe.

The array may contain specific capture nucleotide sequences for each base of a specific locus to be detected. The bases to be detected are present within one or several exons of the same gene nucleotide sequence or from different gene nucleotide sequences.

In a preferred example, the array contains specific capture probes for the detection of SNP in human Cytochromes P450 2C9, 2C19 and 2D6. The array may contain specific capture probes for the detection of several SNP in one gene nucleotide sequence, or the array may contain specific capture probes for the detection of several SNP in different gene nucleotide sequences.

The target nucleotide sequences are labeled during the amplification step. The labeled associated detections are numerous. A review of the different labeling molecules is given in WO 97/27317. They are obtained using either already labelled primer or by incorporation of labelled nucleotides during the amplification step.

Ag/Ab

The method is also particularly useful in the settlement of homogeneous assays. Particularly of interest is the antibody/antigen reaction in which the binding of an antibody (or inversely of an antigen) on its antigen can be followed and measured in the same solution. The present invention avoids the steps of washings and handling as presently performed in the classical ELISA methods. In a preferred embodiment, the assay is a multiplex detection with the antibodies (or the antigen) immobilized on the surface of the wells in the form of an array as described in the U.S. application Ser. No. 10/723,091. Antibodies or antigens can be spotted easily on activated glass and be present in the form of spot which are then used for the reaction with their specific targets being antigens, antibodies or ligands or receptors.

In a particular embodiment, the assay is comparable to the ELISA assay with the protein to be detected being an antigen or an antibody. The reaction is taking place as for ELISA assay and the detection performed by one of the methods suitable for array detection comprising but not limited to fluorescence, bioluminescence or colorimetry.

Real-Time PCR

One embodiment of the invention is to combine in one process the real-time PCR together with the hybridization on capture probes for identification of the target molecules or organisms. The present invention also covers the method, device and apparatus for performing real-time PCR amplification and detection. Preferably the real-time PCR process for identification and quantification of an organism or part of an organism in a sample comprises the steps of: amplifying in a closed device a nucleotide sequence from said organism or part of it in the presence of at least one primer pair which is specific for the nucleotide sequence to be identified and quantified and at least one capture molecule, said capture molecule being immobilized at a given location on an inner surface of the closed device, said inner surface being separated from outer surface by an optically transparent solid support, wherein said solid support has a refractive index higher than the refractive index of the medium where the capture molecule is located, and wherein said capture molecule comprises a capture portion of between 10 and 2000 bases and preferably between 10 and 600 bases and more preferably between 15 and 100 bases able to specifically hybridize to the amplification product. The presence of amplicons in solution is detected by the assay of the amplicons hybridized onto their specific capture molecules during the amplifying procedure by detecting light emitted from the target molecule as a result of excitation of the target molecule by the illumination light beam as provided by the present invention. The detection is performed at least during or after at least 3 and preferably 5 and even more preferably after each of the PCR cycles as for example during the annealing step or in a particular hybridization step incorporated into the 3 temperature steps of the PCR. Preferably the emitted light is detected through said optically transparent solid support at an observation angle, wherein said observation angle is measured relative to the normal versus said solid support surface and is comprised between a critical angle and 90° for a light beam of a wavelength corresponding to the emitted light, wherein said emitted light of the bound target through said support is the result of an evanescence coupling and wherein detected emitted light is not totally internally reflected inside the transparent support. Preferably, the detection is performed by the acquisition of a single image pixels for the overall surface having bound targets. Such pixel information of all targets is obtained simultaneously. This feature allows all target binding to have the same kinetic of binding.

In a particular embodiment, the image is obtained by performed by scanning row by row of the array surface. In a preferred embodiment the process is performed in the same solution and in the same closed device and/or with the same machine device. Preferably the optically transparent solid support comprises a closed chamber for the detection of the bound target in the presence of a solution comprising the target molecule (soluble target molecule). For example, one combines in one process the real-time PCR together with the hybridization on capture molecules for identification of the target molecules or organisms in the same chamber and with the same closed device. The closed device means that the solution is not in fluidic contact with the outside of the device. The device may comprise several elements like chambers connected together but the overall device is closed during the PCR and the detection for the real time PCR on array as provided by the invention. Preferably the method of combining PCR and real time detection for quantification of targets is performed as described in EP 1788097. Preferably the device is made as proposed described in the present invention.

In a preferred embodiment, the process allows the amplification and specific detection of an organism or part of an organism in the presence of possibly 4 and even 20 and even more than 50 other organisms or parts of organisms being present in the same sample. Assays are performed in order to determine if a sample contains or not some targets, but in a given sample the number of targets being effectively present is usually very small even if the assay is designed for the detection of a large number of them. This is the meaning of the term possibly present in the sample. The array built for the detection of such assay will also contain at least 4 and even 20 and even 50 capture probes specific for the binding of the corresponding amplicons from these amplified targets.

In another embodiment, the at least one primer pair is capable of amplifying at least four nucleotide sequences from other organisms so as to produce the amplification products.

In still another embodiment, at least 4 primer pairs are used so as to produce multiple amplification products, said each specific primer pair showing sequence homology of less than about 80% with the other primer pairs specific for at least four nucleotide sequences.

In a particular embodiment, the device comprised the detection solid support with the immobilized capture molecule together with a PCR reaction chamber; The device is settled in order to provide the conditions for performing the PCR amplification cycles within the detection chamber or within the same device so as to have contact between the solution having the formed amplicons and the capture molecules and be able to follow the appearance of the amplicons along the PCR cycles. This is a heterogeneous detection in real-time PCR.

In another embodiment the invention provides a kit comprising a reaction chamber and a thermostable DNA polymerase enzyme that is active at a salt concentration between about 25 mM and about 300 mM. Preferably, the kit also comprises reaction chamber and/or a DNA polymerase and a mix for performing multiplex PCR preferably the QIAGEN Multiplex PCR Master Mix.

In one embodiment, the different parts of the diagnostic and/or quantification apparatus necessary for making the PCR amplification and the detection on the array are integrated into the same apparatus in order to detect the target nucleotide molecule bound on the capture molecules of the array during the PCR cycles of amplification. To read the presence of the nucleotide target bound on the capture molecules means that the detection has to be performed during one of the steps of the PCR itself, or in a step between the cycles. The reading in a preferred embodiment requires the addition of one and preferably two steps to the cycles, one necessary for the denaturation of the double strands amplicons and the other one for the hybridization itself.

In a preferred embodiment, the capture probes for the detection of the amplicons contain a specific portion specific of the amplicons to be detected and a spacer. Preferably the spacer and the specific part of the capture probes are located relative to the hybridized target as proposed in EP1788098A1.

The present method of PCR and detection according to the present invention allows to obtain a molecular method of genomic assay having the following features: The method is fast since the PCR and detection are performed together in a single assay, the method is multiparametric since the use of array allows the detection in a simultaneous assay of multiple targets by specific hybridization of the different amplicons on capture molecules present in different locations on the surface of the device, the method can be made quantitative if the appropriate internal standards are provided, the method has a large dynamic range since different target amounts will be detected at different PCR cycles, the method is easy to use since the device is closed for the assay and the process is performed by the apparatus with no manual intervention necessary, the method avoids PCR contamination since the device is closed during the assay and is not open thereafter thus avoiding contamination of the assay room by the formed amplicons.

Apparatus for Real Time PCR in the Forbidden Angle Detection

The present invention also covers the machine and apparatus necessary for performing the various steps of the process mainly for diagnostic and/or quantification of a (micro) organism or part of an organism possibly present in a sample that comprises the apparatus as provided in the invention and described here above, mainly:

an optically transparent solid support that comprises at least one target molecule bound on capture molecules present on said solid support surface (bound target molecule) and wherein the refractive index of the solid support is higher than the refractive index of the medium where the capture molecule is located; a light source to produce a light beam of wavelength suitable for exciting the target molecule; a detector for measuring light emitted from the target molecule as a result of excitation of the target molecule, said emitted light being detected through said optically transparent solid support at an observation angle, wherein the observation angle is measured relative to the normal versus said solid support surface and is comprised between a critical angle and 90° for a light beam of a wavelength corresponding to the emitted light, wherein the detected emitted light is not totally internally reflected inside the transparent support.

In a preferred embodiment, the apparatus further comprises a device for thermal regulation. In a particular embodiment, the apparatus further comprises an automated thermal cycler capable of alternatively heating and cooling, and adapted to receive at least one reaction chamber containing said immobilized capture molecules, and reagents for nucleic acid amplification.

In another embodiment, the apparatus further comprises a computer program for transforming the measured signal into digital data. Preferably, the computer program recognizes the locations of the array where a signal is formed.

In a preferred embodiment, the detector of the apparatus comprises a CCD camera. In a particular embodiment, the apparatus further comprises a reaction chamber for PCR amplification, such that amplification and detection on the array are integrated into the same apparatus in order to detect the hybridized amplicons during the PCR cycles of amplification.

In a preferred embodiment, the apparatus further comprises means for correcting image distortion, said means comprising a cylindrical lens. In another embodiment, the apparatus further comprises means for increasing the depth of focus, said means comprising a mechanical tilt of the captor surface of the detector relative to the emitted light direction.

The apparatus may further comprise a thermal cycler for carrying out an automated PCR amplification of nucleotide sequences obtained from an organism or part of an organism into double-stranded target nucleotide sequences, said thermal cycler being capable of alternately heating and cooling said support for producing labelled target nucleotides.

A preferred apparatus is one in which the detection is performed during the cycles of the amplification. In a preferred embodiment, the apparatus is used for real-time PCR amplification and detection.

The device for detecting a signal preferably measures bound target nucleotide sequences on their capture molecules at least 2 times during the PCR, preferably 5 times, more preferably more than 10 times.

In an alternative embodiment the device for detecting a signal measures bound target nucleotide sequences on their capture molecules after the cycles of the amplification are completed.

Such method leads to the real-time PCR detection on array. Real-time PCR provides a particular method for the calculation of the target present in the initial sample by measuring the minimum number of cycles necessary for the detection signal to cross a threshold or cut off value (CT).

In an alternative embodiment, the quantification of the amount of nucleotide molecule is performed by measuring the number of thermal cycles necessary to reach a fixed value defined as the threshold (cycle threshold or CT). The threshold cycle is when the system begins to detect the increase in the fluorescent signal associated with an exponential growth of PCR product during the log-linear phase.

There are different methods for the quantification of the amount of target sequence. See for example ABI User Bulletin, (URL "docs.appliedbiosystems.com/search.taf?") or T. Dorak 2006 (in Dorak: Real-Time PCR: Advances Method Series, Oxford: Taylor and Francis, and www-dorak.info/genetics/realtime.html).

The results can be compared to an absolute standard curve. In this embodiment, the quantification of the amount of nucleotide molecule is performed by comparing the number of thermal cycles necessary to reach a fixed value (CT) with a standard curve wherein the CTs are plotted against standard concentrations. Preferably, the standard curve is performed on the same micro-array.

The results can also be compared to a relative standard curve with one of the experimental sample be used as calibrator.

Quantification is also performed by comparing the CT of the target with of a reference nucleotide molecule. The reference nucleotide molecule is preferably amplified in the same solution and detected on the same micro-array as the target nucleotide molecule in order to be able to have similar or identical amplification efficiency.

Device

The invention covers a reagent device for the detection and/or quantification of target molecules containing at least one capture molecule immobilized on an inner surface of the said device (observation area), said inner surface being separated from an outer observation surface by an optically transparent solid support for detection of target molecules along an observation angle (θobin) being a forbidden angle, and wherein said solid support has a refractive index higher than 1.33.

In a preferred embodiment, the array of at least 4 capture molecules is provided at different defined locations (spot) on a surface of a solid support having optical transparent quality having refractive index n1 and a chamber being formed on the surface of the said solid support covering the bound capture molecules and wherein the refractive index of the solid support is higher than the refractive index n2 of the solution present in the said chamber where the binding of the target on the capture molecule occurs and wherein said support having two surfaces inclined relative to the surface of the support on which the capture molecules are bound, one being optically transparent and used for collecting the light emitted from the location of the capture molecules in the forbidden angle (θobin) and the other one opposite being black or covered with a color being black or covered with a color having an absorption corresponding to the wavelength of the emitted light. The θobin relative to the normal to the solid support surface in the support is such that $90°>θobin>\sin^{-1}(n2/1.33)$.

The surface of the optical block is preferably inclined relative to the surface of the support on which the capture molecules and used for collecting the light emitted from the location of the capture molecules has a with of at least 1 mm and better ate least 3 mm and even better 5 mm.

In a particular embodiment, the capture molecules are immobilized on the solid support surface of the optically transparent solid support through a layer of material being of different nature than the optically transparent solid support.

Preferably the device comprises two interconnected chambers between which the liquid do not flow spontaneously but will flow well if submitted to centrifugal force. Preferably the chambers are separated by a spur. The device also comprises an injection chamber having a close system preferably a screw cap which lies preferably between the two flat chambers found on each side of the cartridge. The "optical chamber", has one or more sides being formed by thin walls preferably thinner than 1 mm and more preferably less than 0.5 mm thick and one side being the optical bloc. The other (thin) chamber has walls being preferably walls thinner than 1 mm and even more preferably less than 0.5 mm. Both chambers have preferably a volume of between 10 and 1000 µL and even more preferably between 50 and 200 µL. The optical block is from optical grade material. The surface is preferably perfectly smooth and flat with scratches and dusts being avoided. Preferably the surface is diamond polished. Still preferably the fabrication molding tool for the production of the optical block is ultra polished and preferably nickel coated.

The complete cartridge is preferably created by assembly and laser welding of three plastic parts. The top part contains the threaded feature for the screw cap and the upper enclosures for the flat and optical chambers. The middle part is welded to the upper part and provides the lower enclosure for the thin chamber and has an opening to create the optical chamber when the optical block is welded to it from below. All three parts together with the screw cap form the plastic cartridge.

The solid support is made of a material so that the surface of the optical solid support is maintained flat at temperature higher than 85° C. and wherein said support shows a low self-fluorescence at the wavelength of excitation and emission used for the detection of the target. Preferably the material of the optical block is Zeonex® or Topas® or polyoleline polymers or glass.

The transfer of the liquid from one part to other is preferably obtained by a g-force being applied in one direction or the other by centrifugation. The transfer can also be performed by a pression or pump are other possible embodiments.

In a particular embodiment, the optical block comprises a ridge channel on the opposite side of the support compared to the observation area having immobilized capture molecules.

In a preferred embodiment, the observation area suitable to receive capture molecules is located onto the surface of a support having a series of ridge channels present on another side of the support compared to the immobilized capture molecules. In a particular embodiment, each ridge channel corresponds to a subarray. In a preferred embodiment, the angle of the ridge (β) is equal to 90°. In still a particular embodiment, the device contains several separated observation areas which are distant of each other by 18, 9, 4.5 or even 2.25 mm. Preferably, the observation area is composed of surfaces distant from each other of pitch compatible with the distance of the 24, 96, 384 or even 1536 wells in a multi-well format. Also preferably, each observation area of the multi-well plate has a ridge channel for individual observation of the said area.

In a particular embodiment, the device has the form of a tube with a ridge channel present on the external part of the tube. In a particular embodiment, the device has a ridge channel with one of the surface of the ridge channel being curve so as to correct for the image distortion.

The device is preferably used for real-time PCR amplification and detection.

Kit

The device as described here above comprising a microarray with a plurality of capture molecules immobilized on a solid support surface comprising sequences corresponding to the target nucleic acid sequences to be detected is also part of a kit also comprising an amplification composition having at least one primer pair, a thermostable DNA polymerase, a hot start PCR amplification system, a plurality of dNTPs.

The kit composition also preferably contain a salt composed of a cation and an anion, wherein the said anion has two carboxylic groups and one amine group, wherein the salt concentration in the composition is comprised between 10 mM and 400 mM and an exclusion agent from 1% to 20% by weight.

Reagent Kit

One embodiment of the invention is to combine in one process a PCR together with the hybridization on capture probes for detecting and/or quantifying a target nucleic acid present on a solid support. The present invention also covers a device and reagent kit for performing a PCR amplification and detection. Preferably the reagent kit for detecting and/or quantifying a target nucleic acid present on a solid support comprises: a closed device for the amplification and detection and/or quantification of target nucleic acid containing at least one capture molecule immobilized at a given location on an inner surface of the closed device, said inner surface being separated from outer surface by an optically transparent solid support having a thickness at least equal to d/(2 tan(θobin)), d being the length of observation area and (θobin), the observation angle, and wherein said solid support has a refractive index higher than 1.33, at least one nucleic acid primer; optionally deoxyribonucleotides, optionally an enzyme suitable for the extension of the nucleic acid primer, a fluorescent label, means for detection in a forbidden angle for the presence amplification product at given location.

In a preferred embodiment, the reagent kit further comprises a means for sealing said device during said amplification and detection. Preferably said sealing means is an integrated part of the device which is used for closing the device when the solution is injected into the device. Integrated sealing means is easier to package and to use since it is already integrated into the device when received by the user. It will also provide tight lock preferably having multiple entries for allowing the sample solution to enter or not into different parts or chambers of the device. The multiple entries are preferably the injection entry, the PCR entry and the microarray chamber entry. Preferably the multiple entries are ordered by the position of the lock relative to the device. Preferably, one lock position allows a completely closed and tight micro-array chamber.

In another embodiment the thickness of the support corresponding to said observation angle (θobin) is at least equal to d/(2 tan(θobin)), d being the length of solid support.

In a particular embodiment, the thickness of solid support suitable for detection of amplification products in a forbidden angle is obtained by joining two solid supports of same composition being separated by a material (gel, liquid, oil) having a refractive index close to the refractive index of the solid support.

EXAMPLES

Example 1

Detection of Cy3 Labelled Arrays in Presence or Absence of Cy3 in Solution with Forbidden Angle Technology The Diaglass slides (Eppendorf, Hamburg, Germany) were functionalized for the presence of aldehyde according to the method described in patent application WO02/18288. The protocol described in this patent application was followed for the grafting of aminated DNA to aldehyde derivatized glass. The aminated capture molecules were spotted from solutions at concentrations of 3 μM except the BAT-973 which was spotted at 300 nM. The capture molecules were printed onto microscopic glass slides with a home made robotic device using 250 μm diameter pins. The spots were 400 μm in diameter and the volume dispensed was about 0.5 nl. Slides were dried at room temperature and stored at 4° C. until used.

An array of (6×12 spots) has been spotted with solutions containing 9 different concentrations of Cy3 labelled detection control polynucleotides (SEQ ID NO: 1) (3 μM, 1 μM, 750 nM, 500 nM, 250 nM, 100 nM, 50 nM, 10 nM and 0 nM) in 6 replicates.

SEQ ID NO: 1:
5'NH2-TACCTACTACGCTACACGAACCTACAAGACAAGATAAAGACA

GACTCATG-Cy3 3'

The polynucleotide is Cy3 labelled at 3' end and aminated at 5' end.

We also spotted a 5'-NH2 polynucleotide specific of P35 comprising a capture portion and a spacer portion (underlined):

SEQ ID NO: 2:
5'NH2-ATAAAAAAGTGGGTCTTAGAAATAAATTTCGAAGTGCAATAAT

TATTATTCACAACATTTCGATTTTTGCAACTACTTCAGTTCACTCCAAA

TTAGTCATCCCTTACGTCAGTGGAGATAT-3' at a concentration of 3 µM in 6 replicates as well as a 5'-NH2 polynucleotide specific for EPSPS7 comprising a capture portion and a spacer portion (underlined):

SEQ ID NO: 3:
5'NH2-ATAAAAAAGTGGGTCTTAGAAATAAATTTCGAAGTGCAATAAT

TATTATTCACAACATTTCGATTTTTGCAACTACTTCAGTTCACTCCAAA

TTACTCCTACTCGCCGCCCTGTCCGA-3'.

These polynucleotides were not labeled.

The spots size on the array is around 400 µm diameter. The polynucleotides were spotted in 6 replicates.

After spotting, slides have been washed 1×5 min in SDS 0.05%, 1×1 min in H$_2$O, 1×5 min in NaBH$_4$ solution 2.5 mg/ml of PBS75% and ethanol 25%, then washed again in H$_2$O for 1 min and finally 1×5 min in boiling water. After the washing steps, slides have been dried at room temperature and stored in the dark at 4° C.

An Eppendorf hybridization chamber (Hamburg; Germany) was fixed around the array and tilled with 200 µl of a solution of water containing 0 or 2 µM of Cy3 labeled polynucleotides (SEQ ID NO: 1).

As explained on FIG. 2, the slide was positioned onto an equilateral prism with a drop of glycerol 87% between prism and slide in order to have a layer between prism and slide with the same refraction index as the glass.

The prism and slide were positioned in front of a green argon laser (Spectra-Physics 168B with a 515 nm excitation light. 150 mwatt). The laser beam was enlarged by use of a 3.5× telescope made of two lenses (−50 mm divergent and 175 mm convergent 125 mm apart), then goes through a variable-width slit a few millimeters wide allowing to select a region of interest on the slide. The array was excited on its all surface simultaneously.

The laser have been powered on for 3 sec then turned off and the acquisition of emitted light from the array during these 3 sec (at a gain of 1) has been done with a CCD camera cooled mono 12 bit (#01-RET-OEM-FM-12-C, Qimaging, Canada) positioned at an observation angle of 65° from the normal of the surface of the array slide. The material used in the example was glass having a refractive index of 1.5 and water having a refractive index of 1.33. In this condition the calculated critical angle is given by the formula $\theta=\arcsin(1.33/1.5)=62.4°$ and the possible observation angles according to the invention are greater than 62.4°.

The CCD camera was coupled with imaging software (QCapture version 2.90.1 of Quantitative Imaging Corporation).

The scheme of a complete system is shown on FIG. 2. Quantification of the array has been done using the line profile of Maxime DL software. The quantification of the images obtained with array chamber filled with 0 µM and with 2 µM of Cy3 polynucleotides are shown respectively in FIGS. 5A and 5B. In the forbidden angle, virtually no incident light emitted in the solution was reflected into the camera when positioned in the field of the forbidden angle. However, when the observation was not in the forbidden angle, the signal obtained was saturated (65536) in all the area of the array and it was impossible to detect and to quantify the spots.

This example showed the detection and quantification of the targets when bound to their capture molecule according to the invention. It also demonstrated that even in the presence of high concentrations of Cy3 fluorochrome in solution in the hybridization chamber (FIG. 5B), the array is detected with a sensitivity equivalent to the one obtained in the absence of fluorescent probes in the solution (FIG. 5A).

One particular feature of the invention is the possibility to follow the presence of the fluorescent solution since it is present on the image in a location physically separated from the array.

Example 2

Online Detection of Cy5 Amplicon During Hybridization on Specific Capture Molecule Immobilized onto a Glass Array with the Forbidden Angle Detection Technology An array (5×11) has been prepared as in example 1. The SEQ ID NO: 1 is labelled with Cy5 at 3' end and aminated at 5' end. The polynucleotides spotted are the same with the addition of a polynucleotide specific to *S. aureus* comprising a capture portion and a spacer portion (underlined):

SEQ ID NO: 4:
5'-AACTGCTGGACTTTTTTTAGGTAAGAGGAATTCAAAGTTGAGTCCA

TTTGTGATGCTAGAAAAGTTGGAA-NH2 3' aminated at 3' end. After spotting, slides have been washed 1×5 min in SDS 0.05%, 1×1 min in H$_2$O, 1×5 min in NaBH$_4$ solution 2.5 mg/ml of PBS 75% and ethanol 25%, then washed again in H$_2$O for 1 min and finally 1×5 min in boiling water. After washing steps, slides have been dried at room temperature and stored in the dark at 4° C.

A PCR has been processed to amplify specifically an amplicon of *S. aureus* with 2 primers (PSauF) and (PSauRCy5) with these respective sequences:

PSauF (SEQ ID NO: 5):
5'-GCAGCAGCAATGCGTTA-3'
and

PSauRCy5 (SEQ ID NO: 6):
5'Cy5-GAACCACGACCTGTTTC-3'.

The 1000 µl PCR mix has been prepared and contained PCR buffer 1× (Qiagen, Hilden, Germany), 200 µM of dATP, 200 µM of dCTP, 200 µM of dGTP, 100 µM of dTTP and 300 µM of dUTP, 0.1 µM of PSauF and 0.2 µM of PSauRCy5, 20 U Qiagen Taq polymerase, 20 U of UNG enzyme and $10^6$ copies of the Mu50 plasmid VRSAp containing the following sequence specific of *S. aureus*:

SEQ ID NO: 7:
5'-ATTTTCGCCACTTAATTAGGTGCTAAAATAGCGAATTATACGTTTG

GTAGTTTTAGGTGTACTTTTAATTACATTTAAAACTCTTTATATACGCC

ATTAAAAGTGTTAATATTACTTATAAATAFFAAAAGAGTCGATGCTATF

GGCGTAGCATCGACTCTCGGTAATAAAACGATTCGCACTCGTTTGTTTA

-continued

```
TATATTTTTTTGATACTTGTATTATATATATCTAATCATCTAAGTGCAA

GCACAAAACATATAACTTACGTAAAAATTGTTTTATTACCTCAATCCCA

AAATGGAAATGAGGTTTTTATTATGCCCAATTTTGAAAAATATAATTTA

TCACAAGTAAAAACTGAAAGATTTTATCAACTGCCTAAATATTTATTTG

AAGATGCATATTTTAAGAAAATGTCTGCAGAAGCCAAAATTATGTATGC

GTTATTAAAAGATCGTTTTGAATTATCCCTCCAAAATGAATGGGTAGAT

AAAAATAATAATAMACTTTATTTTCAGTAATAAACATTTGTGTGAATAC

TTAGGTTATGCAGAACAAAAAATTATAAAATTAAAAAAAGAGTTAATAA

AATTTAATTTACTAACTCAAGAACGTGTTGGCCTTAATAAACCAAATAG

ATTATACCTATTAAAACCTAATTATGACATTGAAGCCAGTCATATCAAG

GAACTTCCAAATTCACAGTTCCAGAACAATGAATTTGGAAGTTCTAGAA

CTGTGAATTTAAGTGGTCAAGAACTTCCAAATTCACAGTCTAATGATAC

TGATTATAATGACACTGATTATATTAAGACTAATTATAATGATATGTAT

GATTTGA-3'.
```

The mix has been aliquoted in 100 µl PCR tubes and processed in a Master cycler PCR machine (Eppendorf) with the following program: 22° C. for 10 min, 95° C. for 2 min then 40 cycles made of 3 temperatures: 94° C. for 30 sec, 54° C. for 30 sec and 70° C. for 90 sec, then a last step at 70° C. for 10 min before going down to 4° C. PCR products have been frozen after PCR. 100 µl of hybridization mix has been prepared containing 50 µl of genomic Hybribuffer (Eppendorf, Hamburg, Germany), 45 µl of distilled water and 5 µl of S. aureus Cy5 labelled PCR product.

In situ frame of 65 µl (Eppendorf, Hamburg, Germany) has been fixed around one glass array and filled with 65 µl of hybridization mix and then sealed with a plastic coverslip. On the back side of the hybridization chamber, we fixed a special thermocouple which was temperature controlled. The complete heating process test bench was composed of the following relevant components:

thermocouple: RS-component N° 219-4321 self adhesive thermocouple, type K-nickel Chromium/nickel Aluminium (RS components, Northamptonshire, UK), a transmitter: RS-COMPONENT N° 363-0222 transmitter temperature thermocouple 4_20 mA (RS components, Northamptonshire, UK), a converter: National instruments 7790264-01 USB 6009 48 Ksamples/sec DAQ multifunctions 14 bits for USB (National Instruments, Austin, Tex., USA)

a heater: MINCO heating foil flexible heater: Kapton 0.75"×0.75" HK 5578 R18,3 L12F (Mince, Minneapolis, Minn., USA).

The slide with the chamber has been put in contact with a heating block at 95° C. for 3 min for denaturation with the heated cover heated at 95° C. and then put vertically in contact to a glass prism of 74° angle with the heated cover going down to 60° C. and being fixed until the end of experiment. The contact between slide and prism has been done with a drop of confocal microscope non fluorescent oil (#DIN 58884) with a refraction index of 1.51 at 23° C. (Zeiss, Gottingen, Germany).

As shown on FIG. 2, the prism with the slide on it has been put in front of a 633 nm excitation laser (Melles Griot 05-LHP-991, Helium-neon laser of 35 milliwatt). The laser beam is enlarged by use of a 5× telescope made of two lenses (−50 mm divergent followed by 250 mm convergent 200 mm apart), and is then concentrated to a vertical line by a 200 mm convergent cylindrical lens. The width and intensity can be adjusted by varying the distance between the slide and the cylindrical lens, which is equal in this case to 140 mm.

This laser has been powered on every 3 min for 10 sec (0, 3, 6, 9, 12, 15, 18, 21, 24, 27 and 30 min) and then turned off and the acquisition of emitted light from the array during these 10 sec (at a gain of 10) has been done with a CCD camera cooled mono 12 bit (#01-RET-OEM-FM-12-C, Qimaging, Surey, Canada) positioned at an angle of 69° from the normal of the surface of the array slide. The CCD camera is coupled with imaging software (QCapture version 2.90.1 from Quantitative Imaging Corporation, Surey, Canada).

The scheme of the system is shown on FIG. 2. The images have been collected and quantification of 3 spots is reported in FIG. 6: 1 spot corresponding to EPSPS7 capture probe (SEQ ID NO: 3, negative hybridization control, FIG. 6A), 1 spot corresponding to S. aureus capture probe (SEQ ID NO: 4, positive specific hybridization, FIG. 6B)), and 1 spot of positive detection control (SEQ ID NO: 1, Cy5 probe at 3 µM, FIG. 6C)). The image quantification has been processed using Imagene software program (Biodiscovery. El Segundo, Calif., USA). The mean of the pixels signal inside a circle of 8 pixels in each spot has been calculated for each time of hybridization. A graph showing these signals related to the time of hybridization is shown in FIG. 6.

Example 3

Amplification and Detection in the Same Solution of Amplicons Along Different PCR Cycles An new array containing the same spotted polynucleotides than in example 2 has been prepared.

A PCR has been processed to amplify specifically an amplicon of S. aureus with 2 primers as described in example 2. The 2000 µl PCR mix have been prepared and contained PCR multiplex mix 1× (from Qiagen, Hilden, Germany), 150 µM of dUTP, 0.5 µM of PSauF and 0.5 µM of PSauRCy5, and 10exp7 copies of the Mu50 plasmid VRSAp containing a sequence specific of S. aureus.

The mix has been aliquoted in 100 µl PCR tubes and processed in a Master cycler PCR machine (Eppendorf) with the following program: 95° C. for 15 min, 94° C. for 2 min then 40 cycles made of 3 temperatures: 94° C. for 30 sec, 54° C. for 90 sec and 72° C. for 60 sec, then a last step at 72° C. for 10 min before going down to 4° C. PCR tubes are removed one by one from PCR master cycler after 20 cycles, 25, 30, 35 and 40 cycles.

65 µl of S. aureus Cy5 labeled PCR product from each PCR tube have been hybridized onto the array as described in example 2. The hybridization, the detection and quantification of the signal on the array spots are the same as in example 2. The signals were taken after 2 min of hybridization.

The images have been collected and quantification for 1 replicate of 3 spots is reported in FIG. 7: 1 spot corresponding to EPSPS7 capture probe (SEQ ID NO: 3, negative hybridization control, FIG. 7A), 1 spot corresponding to S. aureus capture probe (SEQ ID NO: 4, positive specific hybridization, FIG. 7B), 1 background spot have been processed using Imagene software program (Biodiscovery, El Segundo, Calif., USA). The mean of the pixels signal inside a circle of 8 pixels in each spot has been calculated for the different PCR cycles. Background spot signal has been subtracted from the signal. A graph showing the signals obtained for 1 replicate of negative hybridization (FIG. 7A) and for 1 replicate of the specific

*S. aureus* positive hybridization (FIG. 7B) in different hybridization reactions containing amplicons coming from the different PCR cycles is shown in FIG. 7.

Example 4

Online Detection of Silver Precipitation Reaction on Gold Labeled Target Molecule Hound onto a Glass Array with the Forbidden Angle Detection Technology An array (10×14) has been spotted as described in example 1 on glass slide with 10 replicates of biotinylated and 5' aminated DNA polynucleotide probes produced by PCR by amplifying a *Chlamydia trachomatis* sequence of 415 base pairs using primer EPCHL01 5'NH2-GAATTCTTAAGT-TCGGTCGG-3' (SEQ ID NO: 8) and primer EPCHL02 (SEQ ID NO: 9) 5'-GAATTCAAAGTTGTCGAGAA-3'. PCR mix contains these 2 primers at a final concentration of 1 µM, dUTP biotinylated at a final concentration of 2.5 nM, dATP 200 µM, dCTP 200 µM, dGTP 200 µM and dTTP 150 µM, Taq polymerase (Eppendorf, Hamburg Germany) at 2 U/100 µl, PCR buffer (Eppendorf, Hamburg, Germany) 1× concentrated and 1 ng of plasmid PCHL1 from *Chlamydia trachomatis* containing the insert of 415 bases. Temperature protocol of PCR was: 5 min at 94° C. then 40 cycles containing a step at 94° C. for 30 see, a step at 52° C. for 30 sec and a step at 72° C. for 30 sec, then 10 min at 72° C. and overnight at 4° C.

The spotting solutions contain the probe at different concentrations: 400 nM, 200 nM, 100 nM, 40 nM, 20 nM, 10 nM, 4 nM, 2 nM, 1 nM, 0.4 nM, 0.2 nM, 0.1 nM, 0 nM, 100 nM. After spotting, slides have been washed as explained in example 1.

Slides have been washed, incubated in a anti-biotin gold conjugate solution rinsed and finally dried following the protocol of Silverquant detection kit (Eppendorf, Hamburg, Germany).

A PVC chamber (Eppendorf, Hamburg Germany) was fixed around the array on the glass slide and the slide was fixed onto a prism with a drop of glycerol 87% between slide and prism as schematically presented in FIG. 2.

Chamber was filled with a mix of Silverquant solutions (Eppendorf, Hamburg, Germany) containing 150 µl of Silverquant solution A and 150 µl of Silverquant solution B.

Slide kept under red laser during 5 min and signal was detected every 10 sec from min 0 to 2 min then every 20 sec from 2 min to 5 min by using the CCD camera (as explained in example 2) with an observation angle of 63' from the normal of the array support).

Images were taken at a gain of 1 with acquisition time of 54 millisec.

The images were collected and quantified for 1 replicate of 9 different concentrations spots (400, 200, 100, 40, 20, 10, 4, 2, 1 nM) using Imagene software program (Biodiscovery, El Segundo, Calif., USA). The mean of the pixels signal inside a circle of 8 pixels in each spot has been calculated for the different spots. A graph showing the kinetic of silver precipitation on spots of different concentrations of detection controls was presented in FIG. 8.

Example 5

Discrimination of Reading Between Signal Bound on Capture Probe and Colored Solution Using Ridge Channel Microstructures An array has been spotted on Diaglass (Eppendorf, Hamburg, Germany) with a biotinylated *Chlamydia trachomatis* sequence 5" aminated at a concentration 100 nM as explained in example 4 with a pin of 250 µm giving spots of 400 µm in diameter and a pitch between spots of 700 µm. After spotting and washing, the biotinylated capture probes have been labeled using the Silverquant detection kit protocol (Eppendorf, Hamburg, Germany).

After labeling, the slide has been put upside down onto a transilluminator and the array on slide has been captured using a Canon camera EOS350 with a lens of 28-80 f 1:3.5-5.6 (Canon, Tokyo, Japan) in an observation angle of 40° from the normal of the array surface.

Then, the array has been surrounded by a chamber filled with a colored solution of Aniline blue 0.001% (Sigma. Bornem. Belgium) and a new picture of the array have been taken with the camera in an angle of observation of 40° from the normal of the array surface.

A layer of glycerol 87% (Sigma, Bornem, Belgium) has been added on the surface of the slide opposite to the array slide and a slide having ridge channel microstructure has been put on the glycerol layer as shown on FIG. 9. The ridge channel microstructure was made with photoactivable resin (CRIF, Gosselies, Belgium) and contains a series of microstructures of 4 mm size between each channel, having an angle at 25° ($\alpha$), an angle at 90° ($\beta$) and the third angle at 65° for each microstructure. Array has again been captured using a camera in an observation angle of 40° from the normal of the array surface and a second picture within the forbidden angle has been taken using the camera in an angle of 65° from the normal of the array surface. This last picture shows the possibility to see the signal of silver precipitate on capture probe without seeing the colored liquid solution when the picture is taken in the forbidden angle in the presence of ridge channel microstructure.

Example 6

Real Time PCR on Array in a Closed Device Performed by Assay of the Amplicons Along the PCR Cycles Using the Detection Method According to the Present Invention An array has been spotted on the surface of a plastic device. The reaction device was a disposable plastic cartridge used for each assay and placed inside the instrument for the PCR, hybridization and detection steps. It comprises three interconnected chambers between which the liquid can flow. The injection chamber is mainly located below the screw cap and lies between the two flat chambers found on each side of the cartridge. Both flat chambers are 10×20 mm in area and 0.5 mm thick. One of the flat chambers is called "thin chamber" or "PCR chamber" because the plastic enclosure—above and below the solution—are only 0.5 mm thick. The other chamber, called the "optical chamber", has one side of the plastic enclosure 0.5 mm thick and the other 3.5 mm being the optical bloc. Both these chambers are designed to hold about 100 µL of solution in each. The optical block is in Zeonex and is from optical grade. The surface is perfectly smooth and flat with scratches and dusts being avoided. The side part opposite to the observation side was covered with a black paint. A figure of the device is provided in FIG. 11.

The complete cartridge is created by assembly and laser welding of three plastic parts. The top part contains the threaded feature for the screw cap and the upper enclosures for the flat and optical chambers. The middle part is welded to the upper part and provides the lower enclosure for the thin chamber and has an opening to create the optical chamber when the optical block is welded to it from below. All three parts together with the screw cap form the plastic cartridge.

The transfer of the liquid from one part to other is obtained by a g-force is applied in one direction or the other by centrifugation.

The plastic devices were activated by plasma treatment for production of epoxy groups on the surface.

The capture nucleotide sequences were printed onto the optical block surface with a home made robotic device using 250 μm diameter pins. The spots have 400 μM in diameter and the volume dispensed is about 0.5 nl. Each capture molecule is potted in triplicate. Devices were dried at room temperature, welded and stored at 20° C. until used.

An array of (21×11 spots) has been spotted with solutions containing 9 different concentrations of Cy5 labelled detection control 5' end amino-polynucleotides (1 μM, 500 nm, 400 nm, 300 nm, 200 nm, 100 nm, 75 nm, 50 nm and 25 nM) in 3 replicates:

(SEQ ID NO. 1)
5'NH2-TACCTACTACGCTACACGAACCTACAAGACAAGATAAAGACAG

ACTCATG-3' Cy5.

Array also contain spotted capture molecules specific of the targets to be detected. A 5'-NH2 polynucleotide specific for *S. aureus* species comprising a capture portion and a spacer portion (underlined):

S. aureus probe:
(SEQ ID NO: 10)
5'NH2-TTATTCACAACATTTCGATTTTTGCAACTACTTCAGTTCACTC

CAAATTATGTTAAGTTATGTGGTGGAATATTCGTTGCCATACCTACCG

C-3' at a concentration of 6 μM in 3 replicates as well as a 5'-NH2 polynucleotide specific for MecA comprising a capture portion and a spacer portion (underlined)

MecA probe:
(SEQ ID NO: 11)
5'NH2-TTATTCACAACATTTCGATTTTTGCAACTACTTCAGTTCACTCC

AAATTACTGCTATCCACCCTCAAACAGGTGAA-3'.

These polynucleotides were not labelled. Other spots specific for other bacterial species such as *H. Influenza, E. aerogenes, K. oxytoca, P. aeruginosa* including the same spacer were also spotted on the array.

After spotting, plastic devices were placed in an oven 30 min at 20° C. under humidity and then at 60° C. 30 min under humidity. Plastic device were then washed 1×5 min in SSC2× pH7 BSA1% SDS 0.1%, 2×1 min in H₂O and finally 1×3 min in boiling water. After the washing steps, plastic device were dried at room temperature and stored in the dark at room temperature.

A PCR has been processed to amplify specifically an amplicon of *S. aureus* and MecA but also some primers specific of other bacterial species:

| Bipartite primers used (SEQ ID Nos: 12-23) | | |
|---|---|---|
| H. influenzae | PHintFA2: | 5'-GGATACCAGTGTCTTGCCAGGTTGCGTGCTTCAACACTAC-3' |
|  | PHintFA1: | 5'-GGATACCAGTGTCTTGCCAGGTACGGCGTTAAACGTCCTAAAG-3' |
| E. aerogenes | PEaerGA2: | 5'-GGATACCAGTGTCTTGCCAGGTACTATTTTCGAACTGCGCAAG-3' |
|  | PEaerGA1: | 5'-GGATACCAGTGTCTTGCCAGGACATTGCCCAGATCCCATG-3 |
| K. oxytoca | PKoxyFA1: | 5'-GGATACCAGTGTCTTGCCAGGTCGGAGTCTTAGTCACCAG-3' |
|  | PKoxyFA2: | 5'-GGATACCAGTGTCTTGCCAGGGCGATGGGTGTTGTACGAG-3' |
| P aeruginosa | PPaerF1A2: | 5'-GGATACCAGTGTCTTGCCAGGTAGCGGTTGATGGGTGTAG-3' |
|  | PPaerF1A1: | 5'-GGATACCAGTGTCTTGCCAGGTCAAGAAGCGTGAAGACGT-3' |
| S. aureus | PSaurGA2: | 5'-GGATACCAGTGTCTTGCCAGGTCAGTCTTACCTGCTCGATTC-3' |
|  | PSaurG1: | 5'-GGATACCAGTGTCTTGCCAGGTGCACGTCTAATACCACTCT-3' |
| MecA | PMecA-A1: | 5'-GGATACCAGTGTCTTGCCAGGAGACGTCATATGAAGGTGTG-3' |
|  | PMec-A2: | 5'-GGATACCAGTGTCTTGCCAGGGATGGCTATCGTGTCACAAT-3' |

The primers also contain a common sequence called the tail sequence. A primers having this tail sequences labelled with Oyster was also added to the PCR.

5' Oyster-GGATACCAGTGTCTTGCCAGG-3' (SEQ ID NO. 24)

The 100 μl PCR mix contained PCR buffer 1× (50 mM TAPS, 95 mM Tris-HCl, 2 mM MgCl₂), 200 μM of dATP. 200 μM of dCTP. 200 μM of dGTP, 100 μM of dTTP, 300 μM of dUTP, 5 nM of each bipartite primers, 300 nM of Tail oyster, 2 U of UNG, 10 U SuperSalt™ Taq Polymerase and $10^6$ copies of the *S. aureus* DNA sample. The buffer also contained glutamate and dextran as explained in EP07150423.7

The mix was placed inside plastic device and processed with RAP-ER instrument (Eppendorf AG, Hamburg, Germany) and based on EP 08006466.0 with the following program: 22° C. for 10 min, 95° C. for 3 min then 6 first cycles made of 3 temperatures: 95° C. for 60 sec, 58° C. for 90 sec, 72° C. for 60 sec, then 38 last cycles made of 3 temperatures: 95° C. for 60 sec, 63° C. for 90 sec. 72° C. for 60 sec.

Every 3 cycles after cycle 20 the annealing time was increased to 5 min and the detection of the targets hybridized onto their specific capture molecule on the array was performed within the forbidden angle with the fluorescent liquid being present in the chamber covering the optical block. The exposure time for the image was 20 sec. Quantification of the array spots was performed using the line profile of MaxIm DL Pro software Version 5.0.

A graph showing the signals of the bound targets related to the PCR cycles is shown in FIG. 13. *S. aureus* and MecA targets are present together in the bacteria and showed indeed the same Ct (cycle 26) even if they result from different target sequences, different amplicons and different probes.

This example showed the detection and quantification of the targets when bound to their capture molecule according to the invention. It also demonstrated the quantification of multiple targets in solution due to the real time PCR assay detected online on array. The same assay was also performed with 17 primer pairs and 17 different capture molecules specific of different bacterial species with the same results. In different experiences, there was no influence of the presence different capture probes being either 4 or 20 or even 50 for the detection of a particular target.

Example 7

Real Time PCR on Array in a Closed Device Performed by Assay of the Amplicons Along the PCR Cycles Using the Detection Method According in the Forbidden Angle The device and its activation and spotting were processed as in example 6. The array contained the same spotted polynucleotide Cy5 labelled at 3' end and aminated at 5' end as in example 6.

A 5'-NH2 polynucleotide capture molecule specific for *P. aeruginosa* was also spotted, comprising a capture portion and a spacer portion (underlined):

```
P. aeruginosa probe:
                                               (SEQ ID NO: 25)
5'NH2-TTATTCACAACATTTCGATTTTTGCAACTACTTCAGTTCACT

CCAAATTACCCAACCCCCGAGGACCTTATTGTGG-3'
``` at a concentration of 6 µM in 3 replicates. The spots size on the array is around 400 µm diameter.

After spotting, plastic device have been washed as described in example 6.

A PCR has been processed to amplify specifically an amplicon of *P. aeruginosa* with 2 primers

```
PPaerF1-AAA8:
                                           (SEQ ID NO: 26)
5'Oyster-TAGCGGTTGATGGGTGTAG-3'

PPaerF1-NAA1:
                                           (SEQ ID NO: 27)
5'-TCAAGAAGCGTGAAGACGT-3'
```

The PCR was performed as in example 6.

Four experiments were performed with different amount of *P. aeruginosa* DNA corresponding to $10^5$, $10^4$ or $10^3$ copies of genome.

Every 3 cycles after cycle 20, the annealing time was increased to 5 min and the liquid was centrifuged from the chamber containing the optical block to the other thin chamber and the detection of the targets hybridized onto their specific capture molecule on the array was performed within the forbidden angle in the chamber covering the optical block. The exposure time for the image was 20 sec.

The images were collected and quantified. Quantification of the array was done using the Quant software and the line profile of MaxIm DL software. A graph showing the signals related to the PCR cycles is shown in FIG. 14. The graph C1, C2 and C3 correspond to the PCR performed with respectively $10^3$, $10^4$ and $10^5$ copies of genome.

For the same target, different concentration have a ct in agreement with theory (10 copies=3 cycles).

---

The invention claimed is:

1. An apparatus for detection and/or quantification of different target molecules being bound at different locations of a surface of an optically transparent solid support, said apparatus comprising:
   (a) an optically transparent solid support having refractive index n1 that comprises (i) at least four target molecules bound on capture molecules present at defined locations on said solid support surface in the form of an array, (ii) a side which is inclined relative to the surface of the support on which the target molecules are bound and, (iii) a chamber being formed on the surface of the solid support forming a device covering the bound capture molecules and wherein the refractive index of the solid support is higher than 1.33,
   (b) a light source to produce a light beam that reaches the surface of the support having immobilized capture molecules with an angle of 90° plus or minus 10°, said light beam being capable of homogeneous excitation of the surface of the support on which the target molecules are bound,
   (c) a lens located on the emitted light path between the surface of the support on which the target molecules are bound and a detector, and
   (d) a detector, positioned at an observation angle $\theta_{obin}$ relative to the normal of said solid support surface, such that $90° > \theta_{obin} > \sin^{-1}(n2/n1)$, n2 being the refractive index of a solution in contact with the solid support, for measuring light emitted from the target molecules in at least four different locations as an image of at least 4 different locations that are spatially discriminated and simultaneously obtained onto the surface of the detector, said emitted light being collected through the side of said support which is inclined relative to the surface of the support on which the target molecules are bound, and wherein said emitted light is focused on the detector surface and is in focus for at least 4 different locations.

2. The apparatus of claim 1, wherein the detector has at least 10 pixels and the surface corresponding to a first location has at least 1 pixel difference from a second location.

3. The apparatus of claim 1, wherein the detector is a camera or a planned detector having at least 10 pixels on which the image is projected.

4. The apparatus of claim 1, wherein the image of the overall surface of the support having bound targets is in focus and projected at once onto the detector surface so that pixels data is attributed to the different locations having bound targets.

5. The apparatus of claim 1, wherein a surface opposite to the side of the support which is inclined relative to the surface of the support on which the target molecules are bound is black or covered with a color being black or covered with a color having an absorption corresponding to the wavelength of the emitted light.

6. The apparatus of claim 5 wherein the solid support has a thickness of at least 1 mm and wherein the side of said support which is inclined relative to the surface of the support on which the target molecules are bound is optically transparent and inclined by an angle of between 90 and 60° relative to the surface of the support on which the target molecules are bound.

7. The apparatus of claim 1, further comprising an automated thermal cycler capable of alternatively heating and cooling, and adapted to receive at least one closed reaction chamber containing said immobilized capture molecules, and reagents for nucleic acid amplification.

8. The apparatus of claim 1, further comprising means for correcting image distortion.

9. The apparatus of claim 1, further comprising means for increasing the depth of focus, said means comprising a mechanical tilt of the captor surface of the detector relative to the emitted light direction.

10. The apparatus of claim 1, further comprising a closing system.

11. A kit for PCR amplification and detection of target nucleic acid sequences comprising:
   (a) an amplification composition having at least one primer pair, a thermostable DNA polymerase, a hot start PCR amplification system, and a plurality of dNTPs, and
   (b) an apparatus according to any one of claims 1-9.

12. The kit according to claim 11, wherein the amplification composition also contains between 10 mM and 400 mM glutamate and an exclusion agent from 1% to 20% by weight.

* * * * *

SEQUENCE LISTING

```
<160> NUMBER OF SEQ ID NOS: 27

<210> SEQ ID NO 1
<211> LENGTH: 50
<212> TYPE: DNA
<213> ORGANISM: Artificial
<220> FEATURE:
<223> OTHER INFORMATION: Chemically synthesized

<400> SEQUENCE: 1
tacctactac gctacacgaa cctacaagac aagataaaga cagactcatg          50

<210> SEQ ID NO 2
<211> LENGTH: 121
<212> TYPE: DNA
<213> ORGANISM: Artificial
<220> FEATURE:
<223> OTHER INFORMATION: Chemically synthesized

<400> SEQUENCE: 2
ataaaaaagt gggtcttaga aataaatttc gaagtgcaat aattattatt cacaacattt     60
cgatttttgc aactacttca gttcactcca aattagtcat cccttacgtc agtggagata    120
t                                                                    121

<210> SEQ ID NO 3
<211> LENGTH: 118
```

```
<212> TYPE: DNA
<213> ORGANISM: Artificial
<220> FEATURE:
<223> OTHER INFORMATION: Chemically synthesized

<400> SEQUENCE: 3
ataaaaaagt gggtcttaga aataaatttc gaagtgcaat aattattatt cacaacattt    60 cgattttttgc aactacttca gttcactcca aattactcct actcgccgcc ctgtccga   118

<210> SEQ ID NO 4
<211> LENGTH: 70
<212> TYPE: DNA
<213> ORGANISM: Artificial
<220> FEATURE:
<223> OTHER INFORMATION: Chemically synthesized

<400> SEQUENCE: 4
aactgctgga cttttttag gtaagaggaa ttcaaagttg agtccatttg tgatgctaga    60
aaagttggaa                                                          70

<210> SEQ ID NO 5
<211> LENGTH: 17
<212> TYPE: DNA
<213> ORGANISM: Artificial
<220> FEATURE:
<223> OTHER INFORMATION: Chemically synthesized

<400> SEQUENCE: 5
gcagcagcaa tgcgtta                                                  17

<210> SEQ ID NO 6
<211> LENGTH: 17
<212> TYPE: DNA
<213> ORGANISM: Artificial
<220> FEATURE:
<223> OTHER INFORMATION: Chemically synthesized

<400> SEQUENCE: 6
gaaccacgac ctgttttc                                                 17

<210> SEQ ID NO 7
<211> LENGTH: 839
<212> TYPE: DNA
<213> ORGANISM: Staphylococcus aureus

<400> SEQUENCE: 7
attttcgcca cttaattagg tgctaaaata gcgaattata cgtttggtag ttttaggtgt    60
acttttaatt acatttaaaa ctctttatat acgccattaa aagtgttaat attacttata   120
aatattaaaa gagtcgatgc tattggcgta gcatcgactc tcggtaataa aacgattcgc   180 actcgttttgt ttatatattt ttttgatact tgtattatat atatctaatc atctaagtgc   240
aagcacaaaa catataactt acgtaaaaat tgttttatta cctcaatccc aaaatggaaa   300
tgaggttttt attatgccca attttgaaaa atataattta tcacaagtaa aaactgaaag   360
attttatcaa ctgcctaaat atttatttga agatgcatat tttaagaaaa tgtctgcaga   420
agccaaaatt atgtatgcgt tattaaaaga tcgttttgaa ttatccctcc aaaatgaatg   480
ggtagataaa aataataata tttacttttat tttcagtaat aaacatttgt gtgaatactt   540
aggttatgca gaacaaaaaa ttataaaatt aaaaaaagag ttaataaaat ttaatttact   600
aactcaagaa cgtgttggcc ttaataaacc aaatagatta tacctattaa aacctaatta   660
tgacattgaa gccagtcata tcaaggaact tccaaattca cagttccaga acaatgaatt   720
```

```
tggaagttct agaactgtga atttaagtgg tcaagaactt ccaaattcac agtctaatga      780
tactgattat aatgacactg attatattaa gactaattat aatgatatgt atgatttga       839

<210> SEQ ID NO 8
<211> LENGTH: 20
<212> TYPE: DNA
<213> ORGANISM: Artificial
<220> FEATURE:
<223> OTHER INFORMATION: Chemically synthesized

<400> SEQUENCE: 8
gaattcttaa gttcggtcgg                                                   20

<210> SEQ ID NO 9
<211> LENGTH: 20
<212> TYPE: DNA
<213> ORGANISM: Artificial
<220> FEATURE:
<223> OTHER INFORMATION: Chemically synthesized

<400> SEQUENCE: 9
gaattcaaag ttgtcgagaa                                                   20

<210> SEQ ID NO 10
<211> LENGTH: 92
<212> TYPE: DNA
<213> ORGANISM: Artificial
<220> FEATURE:
<223> OTHER INFORMATION: Chemically synthesized

<400> SEQUENCE: 10
ttattcacaa catttcgatt tttgcaacta cttcagttca ctccaaatta tgttaagtta      60
tgtggtggaa tattcgttgc catacctacc gc                                    92

<210> SEQ ID NO 11
<211> LENGTH: 76
<212> TYPE: DNA
<213> ORGANISM: Artificial
<220> FEATURE:
<223> OTHER INFORMATION: Chemically synthesized

<400> SEQUENCE: 11
ttattcacaa catttcgatt tttgcaacta cttcagttca ctccaaatta ctgctatcca      60
ccctcaaaca ggtgaa                                                      76

<210> SEQ ID NO 12
<211> LENGTH: 40
<212> TYPE: DNA
<213> ORGANISM: Artificial
<220> FEATURE:
<223> OTHER INFORMATION: Chemically synthesized

<400> SEQUENCE: 12
ggataccagt gtcttgccag gttgcgtgct tcaacactac                             40

<210> SEQ ID NO 13
<211> LENGTH: 43
<212> TYPE: DNA
<213> ORGANISM: Artificial
<220> FEATURE:
<223> OTHER INFORMATION: Chemically synthesized

<400> SEQUENCE: 13
ggataccagt gtcttgccag gtacggcgtt aaacgtccta agg                         43
```

<210> SEQ ID NO 14
<211> LENGTH: 43
<212> TYPE: DNA
<213> ORGANISM: Artificial
<220> FEATURE:
<223> OTHER INFORMATION: Chemically synthesized

<400> SEQUENCE: 14
ggataccagt gtcttgccag gtactatttt cgaactgcgc aag         43

<210> SEQ ID NO 15
<211> LENGTH: 40
<212> TYPE: DNA
<213> ORGANISM: Artificial
<220> FEATURE:
<223> OTHER INFORMATION: Chemically synthesized

<400> SEQUENCE: 15
ggataccagt gtcttgccag gacattgccc agatcccatg            40

<210> SEQ ID NO 16
<211> LENGTH: 40
<212> TYPE: DNA
<213> ORGANISM: Artificial
<220> FEATURE:
<223> OTHER INFORMATION: Chemically synthesized

<400> SEQUENCE: 16
ggataccagt gtcttgccag gtcggagtct tagtcaccag            40

<210> SEQ ID NO 17
<211> LENGTH: 40
<212> TYPE: DNA
<213> ORGANISM: Artificial
<220> FEATURE:
<223> OTHER INFORMATION: Chemically synthesized

<400> SEQUENCE: 17
ggataccagt gtcttgccag ggcgatgggt gttgtacgag            40

<210> SEQ ID NO 18
<211> LENGTH: 40
<212> TYPE: DNA
<213> ORGANISM: Artificial
<220> FEATURE:
<223> OTHER INFORMATION: Chemically synthesized

<400> SEQUENCE: 18
ggataccagt gtcttgccag gtagcggttg atgggtgtag            40

<210> SEQ ID NO 19
<211> LENGTH: 40
<212> TYPE: DNA
<213> ORGANISM: Artificial
<220> FEATURE:
<223> OTHER INFORMATION: Chemically synthesized

<400> SEQUENCE: 19
ggataccagt gtcttgccag gtcaagaagc gtgaagacgt            40

<210> SEQ ID NO 20
<211> LENGTH: 42
<212> TYPE: DNA
<213> ORGANISM: Artificial
<220> FEATURE:
<223> OTHER INFORMATION: Chemically synthesized

```
<400> SEQUENCE: 20
ggataccagt gtcttgccag gtcagtctta cctgctcgat tc                    42

<210> SEQ ID NO 21
<211> LENGTH: 41
<212> TYPE: DNA
<213> ORGANISM: Artificial
<220> FEATURE:
<223> OTHER INFORMATION: Chemically synthesized

<400> SEQUENCE: 21
ggataccagt gtcttgccag gtgcacgtct aataccactc t                     41

<210> SEQ ID NO 22
<211> LENGTH: 41
<212> TYPE: DNA
<213> ORGANISM: Artificial
<220> FEATURE:
<223> OTHER INFORMATION: Chemically synthesized

<400> SEQUENCE: 22
ggataccagt gtcttgccag gagacgtcat atgaaggtgt g                     41

<210> SEQ ID NO 23
<211> LENGTH: 41
<212> TYPE: DNA
<213> ORGANISM: Artificial
<220> FEATURE:
<223> OTHER INFORMATION: Chemically synthesized

<400> SEQUENCE: 23
ggataccagt gtcttgccag ggatggctat cgtgtcacaa t                     41

<210> SEQ ID NO 24
<211> LENGTH: 21
<212> TYPE: DNA
<213> ORGANISM: Artificial
<220> FEATURE:
<223> OTHER INFORMATION: Chemically synthesized

<400> SEQUENCE: 24
ggataccagt gtcttgccag g                                           21

<210> SEQ ID NO 25
<211> LENGTH: 76
<212> TYPE: DNA
<213> ORGANISM: Artificial
<220> FEATURE:
<223> OTHER INFORMATION: Chemically synthesized

<400> SEQUENCE: 25
ttattcacaa catttcgatt tttgcaacta cttcagttca ctccaaatta cccaacccccc  60 gaggaccttta ttgtgg                                                76

<210> SEQ ID NO 26
<211> LENGTH: 19
<212> TYPE: DNA
<213> ORGANISM: Artificial
<220> FEATURE:
<223> OTHER INFORMATION: Chemically synthesized

<400> SEQUENCE: 26
tagcggttga tgggtgtag                                              19
```

```
<210> SEQ ID NO 27
<211> LENGTH: 19
<212> TYPE: DNA
<213> ORGANISM: Artificial
<220> FEATURE:
<223> OTHER INFORMATION: Chemically synthesized

<400> SEQUENCE: 27
tcaagaagcg tgaagacgt                                                19
```